United States Patent [19]

Phillipps et al.

[11] 3,952,031

[45] Apr. 20, 1976

[54] ANAESTHETIC COMPOSITION CONTAINING A STEROID OF THE 5α-PREGNANE SERIES AND METHOD OF USING SAME

[75] Inventors: Gordon Hanley Phillipps, Wembley; Christopher Earle Newall, Acton; Barry Edward Ayres, Amersham, all of England

[73] Assignee: Glaxo Laboratories Limited, Greenford, England

[22] Filed: Dec. 13, 1974

[21] Appl. No.: 532,612

Related U.S. Application Data

[62] Division of Ser. No. 197,915, Nov. 11, 1971, Pat. No. 3,869,451.

[30] Foreign Application Priority Data

Nov. 12, 1970 United Kingdom............... 53911/70

[52] U.S. Cl............................ 260/397.45; 424/243; 260/239.5; 260/349; 260/397.4; 260/239.55 R
[51] Int. Cl.²......................................... C07J 71/00
[58] Field of Search...................... 260/397.45, 239.5

[56] References Cited
UNITED STATES PATENTS

3,822,297   7/1974   Phillipps et al. ............... 260/397.45
3,869,451   3/1975   Phillipps et al. ............... 260/397.45

*Primary Examiner*—Elbert L. Roberts
*Attorney, Agent, or Firm*—Bacon & Thomas

[57] ABSTRACT

This invention relates to steroids of the pregnane and 19-norpregnane series having anaesthetic properties and compositions containing them. More particularly the present invention relates to such steroids having a variety of substituents in the 2β-position, a 3α-hydroxy group and a 5α-hydrogen atom and esters and 20-ketals thereof. At the 11-position of such steroids is preferably either two hydrogen atoms or an oxo group. The compounds according to the invention may conveniently be prepared by reaction of an appropriate 2α,3α-epoxy-pregnane or 19-norpregnane with a reagent which introduces the desired 2β-substituent and various modifications of the compound produced are described to produce compounds within the scope of the invention. The present invention provides compositions containing certain steroids of the pregnane and 19-norpregnane series and such compositions generally may be administered intravenously to induce anaesthesia, the invention providing methods of inducing anaesthesia.

8 Claims, No Drawings

ANAESTHETIC COMPOSITION CONTAINING A STEROID OF THE 5α-PREGNANE SERIES AND METHOD OF USING SAME

This application is a division of application Ser. No. 197,915, filed Nov. 11, 1971, and now U.S. Pat. No. 3,869,451.

This invention is concerned with improvements in or relating to compounds of the pregnane series having useful anaesthetic activity.

It has long been known that a number of steroids give rise to profound depression of the central nervous system and act pharmacodynamically as anaesthetics or hypnotics. Such compounds have been the subject of considerable study in an attempt to find anaesthetics to replace such substances as thiopentone sodium normally used but well known to be accompanied by some degree of hazard and disadvantage. The literature shows that very many steroid compounds have been studied in this regard. Reviews and discussions of some of the work carried out are to be found, for example, in "Methods in Hormone Research" (Edited by Ralph I. Dorfman, Vol. III, Part A, Academic Press London and New York 1964, pages 415–475); H. Witzel, Z. Vitamin HormonFermentforsch 1959, 10, 46–74; H. Selye, Endocrinology, 1942, 30, 437–453; S. K. Figdor et al., J. Pharmacol, Exptl. Therap., 1957, 119, 299–309 and Atkinson et al., J. Med. Chem. 1965, 8, 426–432.

A thorough review of the literature indicates that anaesthetic steroids generally possess poor activity and/or long induction periods. With such compounds a variety of undesired side effects such as paraesthesia and vein damage have also been noted. Steriods possessing anaesthetic activity hitherto described are generally relatively simple pregnane derivatives; often hydroxylated in the 3-position, the general trend having been in the latter case to study 3β-hydroxy compounds in preference to 3α-hydroxy compounds.

We have now found that certain 3α-hydroxy-2β substituted compounds of the pregnane series, which are more particularly described hereinafter, have remarkable anaesthetic properties.

The aforesaid 3α-hydroxy-2β-substituted pregnanes may be generally characterised as being steroids of the 5α-pregnane series having anaesthetic properties and possessing a hydroxy group in the α-configuration at the 3-position, an oxo group at the 20-position, and either two hydrogen atoms or an oxo group at the 11-position, such compounds being further characterised by a substituent R at the 2-position in the β-configuration as more particularly set out hereinafter.

The expression "pregnane series" as used above includes not only compounds of the conventional pregnane ring structure but also the corresponding 19-nor compounds, the presence or absence of a methyl group at the 10-position having little influence on anaesthetic properties.

The 3α-hydroxy-2β-substituted pregnanes which we have found to have especially valuable anaesthetic activity are the 3α-hydroxy steroids of the pregnane and 19-norpregnane series possessing hydrogen atoms in the 5α- and 17α-positions; two hydrogen atoms or an oxo group in the 11-position; an oxo group in the 20-position; and a substituent R (which is an acyloxy, ether, thioether, alkyl, cycloalkyl, aryl, aralkyl, hydroxy, thiocyanato, nitro-oxy or halo substituent) in the 2β-position.

The above 3α-hydroxy steroids may alternatively carry at the 2β-position an azido, sulphonyloxy (e.g. tosyloxy) group, or acylthio group.

The substituent R at the 2β-position in the above-defined 3α-hydroxy-2β-substituted pregnanes may for example be an acyloxy, ether, thioether, alkyl or cycloalkyl group, for example containing up to 9 carbon atoms, a monocyclic aryl group (e.g. a phenyl group) or a monocyclic aralkyl group (e.g. a benzyl group). Acyloxy substituents, which may be saturated or unsaturated, include lower ($C_1$–$C_6$) alkanoyloxy groups, (substituted if desired, for example with one or more halogen, e.g. chlorine atoms, hydroxy, lower alkoxy, amino and substituted amino groups), aroyloxy groups, e.g. a benzoyloxy group or aralkanoyloxy groups, e.g. a phenylacetoxy group. Ether substituents, which may be saturated or unsaturated, include lower ($C_1$–$C_6$) alkoxy groups, lower alkenyloxy groups (e.g. an allyloxy group), cycloalkoxy groups, e.g. a cyclohexyloxy group, aryloxy groups, e.g. a phenoxy group and aralkoxy groups, e.g. a benzyloxy group Thioether groups corresponding to the lastmentioned oxygen groups are representative of 2β-thioether substituents.

Examples of alkyl groups include especially lower alkyl groups containing 1–5 carbon atoms such as methyl, ethyl, propyl, butyl, isobutyl and t-butyl groups. An example of a cycloalkyl group is a cyclohexyl group.

Examples of lower alkanoyloxy 2β-substituents include acetoxy, propionyloxy, butyryloxy, piperidinoacetoxy, morpholinoacetoxy, diethylaminoacetoxy and chloroacetoxy groups. Examples of lower alkoxy groups include methoxy, ethoxy, propoxy, isopropoxy, n-butoxy and t-butoxy groups, the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino, e.g. morpholino groups, or a substituted or unsubstituted acyloxy e.g. morpholinoacetoxy, chloroacetoxy or diethylaminoacetoxy group or heterocyclic groups, e.g. a tetrahydrofuranyl group. Alkyl, cycloalkyl and aryl groups may also be substituted.

As will be seen the above-defined 3α-hydroxy 2β-substituted pregnane anaesthetics conform generally to the following skeletal structure:

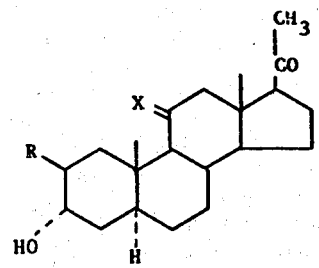

wherein R is a 2β-substituent as above defined and X represents two hydrogen atoms or an oxo group.

The above-defined 3α-hydroxy-2β-substituted5α-pregnane anaesthetics have been found to induce anaesthesia with generally short induction periods, in general the anaesthetic action at suitable doses being indeed instantaneous; the compounds are thus excellent anaesthetics for inducing anaesthesia which is to be maintained e.g. by an inhalation anaesthetic such as ether, halothane, nitrous oxide, trichloroethylene etc. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to a particularly low order of undesired side-effects as compared with previously described steroidal anaesthetics.

The invention further includes $3\alpha$-esters of the above defined $3\alpha$-hydroxy-$2\beta$-substituted-$5\alpha$-20-keto-pregnane compounds particularly lower alkanoyl esters, for example containing in the alkanoyl group up to 5 carbon atoms. Such esters may also be esters containing one or more substituents in the alkanoyl portion e.g. halogen atoms (e.g. fluorine and chlorine atoms), carboxy groups or amino or substituted amino, e.g. diethylamino groups etc. The invention additionally extends to 20-ketals, for example ethylene ketals, of the above $3\alpha$-hydroxy anaesthetics and their esters. Generally the induction period with a 3-ester or a 20-ketal is longer than that with a corresponding $3\alpha$-hydroxy 20-ketopregnane compounds. Both the $3\alpha$-hydroxy compounds and the corresponding 3-esters and 20-ketals may be regarded as central nervous system depressants and thus in suitable doses may also be used as hypnotics or sedatives.

The above-defined $3\alpha$-hydroxy-$2\beta$-substituted$5\alpha$-pregnane anaesthetic steroids and the corresponding $3\alpha$-esters and 20-ketals are hereinafter collectively referred to as $3\alpha$-oxygenated-$2\beta$substituted-$5\alpha$-pregnane anaesthetics.

The above-defined $3\alpha$-oxygenated-$2\beta$-substituted$5\alpha$-pregnane anaesthetics may contain further substitution for example at the 16 and 21-positions. Thus the 16-position may be substituted by one or two lower alkyl groups e.g. methyl groups, a lower alkoxy group e.g. a methoxy group, or by a halogen atom e.g. fluorine or chlorine. The configuration of the 16-substituent may be $\alpha$- or $\beta$-. The 21-position may for example be substituted by alkanoyloxy ($C_{1-8}$) groups e.g. an acetoxy group, or by halogen e.g. bromine.

The various substituents in the steroids according to the invention of the pregnane and 19-norpregnane series may if desired be themselves substituted by substituents which confer water solubility, e.g. amino and substituted amino groups in salt form, or carboxylate groups.

The $3\alpha$-oxygenated-$2\beta$-substituted-$5\alpha$-pregnane anaesthetics may be formulated as convenient, following generally known pharmaceutical practices, with the aid of one or more pharmaceutical carriers or excipients. By the term 'pharmaceutical' as used herein we include applications to both human and veterinary medicine. For anaesthetic purposes the steroids will normally be given by injection and thus one aspect of this invention comprises an anaesthetic composition for parenteral administration comprising a $3\alpha$-oxygenated-$2\beta$-substituted pregnane compound as above-defined in a parenterally acceptable vehicle.

The $3\alpha$-oxygenated-$2\beta$-substituted-$5\alpha$-pregnane anaesthetics are generally new compounds with the exception of $2\beta$-thiocyanato-$3\alpha$-hydroxy-$5\alpha$-pregnan20-one, the new compounds comprising a further aspect of the invention. Generally the 11-oxo compounds possess better anaesthetic properties in terms of induction time and/or degree of action than the corresponding 11-unsubstituted compound.

Particularly preferred new compounds according to the invention by virtue of their excellent anaesthetic properties and short induction period are the following:

$2\beta$-methoxy-$3\alpha$-hydroxy-$5\alpha$-pregnane-11,20-dione,
$2\beta$-ethoxy-$3\alpha$-hydroxy-$5\alpha$-pregnane-11,20-dione,
$2\beta$-isopropoxy-$3\alpha$-hydroxy-$5\alpha$-pregnane-11,20-dione,
$2\beta$-n-propoxy-$3\alpha$-hydroxy-$5\alpha$-pregnane-11,20-dione,
$2\beta$-(2-chloroethoxy)-$3\alpha$-hydroxy-$5\alpha$-pregnane-11,20dione. $2\beta$-methyl-$3\alpha$-hydroxy-$5\alpha$-pregnane-11,20-dione,
$2\beta$-bromo-$3\alpha$-hydroxy-$5\alpha$-pregnane-11,20-dione,
$2\beta$-chloro-$3\alpha$-hydroxy-$5\alpha$-pregnane-11,20-dione,
$2\beta$-iodo-$3\alpha$-hydroxy-$5\alpha$-pregnane-11,20-dione,
$2\beta$-thiocyanato-$3\alpha$-hydroxy-$5\alpha$-pregnane-11,20-dione,
$2\beta$-acetoxy-$3\alpha$-hydroxy-$5\alpha$-pregnane-11,20-dione,
$2\beta$-ethoxy-$3\alpha$-hydroxy-19-nor-$5\alpha$-pregnane-11,20-dione,
$2\beta$-chloropropoxy-$3\alpha$-hydroxy-$5\alpha$-pregnane-11,20-dione,
$3\alpha$-hydroxy-$2\beta$-piperidinoacetoxy-$5\alpha$-pregnane-11,20-dione citrate,
$3\alpha$-hydroxy-$2\beta$-propionyloxy-$5\alpha$-pregnane-11,20-dione,
$2\beta$-n-butoxy-$3\alpha$-hydroxy-$5\alpha$-pregnane-11,20-dione, and
$2\beta$-n-butyl-$3\alpha$-hydroxy-$5\alpha$-pregnane-11,20-dione.

Many of the $3\alpha$-oxygenated-$2\beta$-substituted-$5\alpha$pregnane anaesthetics are poorly soluble in water. We have found however that they may be formulated for parenteral administration in an aqueous solution of a parenterally acceptable non-ionic surface active agent.

The non-ionic surface active agents used for the purpose of this invention are generally those of the water soluble type, conveniently having an HLB value of at least 9, preferably at least about 12, advantageously at least about 13. Preferably the HLB value of the surface active agent is not greater than about 15 although it may, for example, be as high as 18. The surface active agent must naturally be one which is physiologically compatible, i.e. of itself give rise to no physiologically unacceptable side effects in the dosages employed in the intended species to be treated (man or animal). Surface active agents for use in accordance with the invention are for example to be found among the following non-ionic surfactants and classes of surfactants: Polyoxyethylated derivatives of fatty (C12–C20) glyceride oils, e.g. castor oil, containing from 35 to 45 oxyethylene groups, per mole of fatty oil. Polyoxyethylene ethers (containing from 10 to 30 oxyethylene groups) of long chain alcohols (containing for example from 12–18 carbon atoms).

Polyoxyethylene-polyoxypropylene ethers containing from 15 to 35 and from 15 to 30 oxyethylene and oxypropylene groups respectively. Polyoxyethylene ethers (containing from 6 to 12 oxyethylene groups) of alkyl phenols the alkyl groups of which preferably contain 6–10 carbon atoms.

Polyoxyethylated (containing from 15 to 30 oxyethylene groups) fatty acid (e.g. C12–18) esters of sugar alcohol anhydrides e.g. sorbitan or mannitan. Long chain (e.g. C10–16) alkanoyl mono- and di-alkanolamides (the alkanol portions of which for example contain 1–5 carbon atoms) for example lauroyl mono- and di-ethanolamides. Polyethylene glycol esters (containing from 6–40 ethylene oxide units) of long chain fatty acids containing, for example, 12–18 carbon atoms, e.g. polyethylene glycol monooleate (containing for example 8 ethylene oxide units).

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units;

Tween 60, polyoxyethylene sorbitan monostearate containing about 20 ethylene oxide units; and Tween 40, polyoxyethylene sorbitan monopalmitate containing about 20 ethyleneoxide units.

The expression "solutions" is used herein to denote liquids which have the appearance of true solutions and are thus optically clear and capable of passage, for example, through a micro-porous filter, irrespective of whether such solutions are true solutions in the classical chemical sense and irrespective of whether they are stable or metastable. Thus it may be that the steroid is associated with micelles. The solutions of this invention, irrespective of their precise physical nature, behave as true solutions for the practical purpose of intravenous injection.

The proportion of surface active agent to be used in the compositions of this invention depends upon its nature and upon the concentration of steroid desired in the final composition.

In preferred compositions according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition.

As will be clear, the proportion of steroid in the aqueous solution according to the invention depends upon the nature and amount of surface active agent used. The composition will generally contain at least 1 mg/ml of steroid and solutions can be made containing for example up to 6–7 mg/ml of steroid or even 10 mg/ml.

In a preferred method of preparing the solutions according to the invention the steroid is first dissolved in the selected surfactant for example, with heating and the resulting solution dissolved in water. Alternatively the steroid may be dissolved in a volatile organic solvent advantageously having a boiling point of less than about 80°C which is miscible with the surface active agent such as a volatile lower aliphatic ketone e.g. acetone or methyl ethyl ketone or a volatile halogenated hydrocarbon e.g. chloroform or methylene chloride. Acetone is particularly preferred for this purpose. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steroid with an aqueous solution of the surface active agent.

In all cases simple tests enable one to determine the relative proportions of surface active agent required.

Naturally those $3\alpha$-oxygenated-$2\beta$-substituted-$5\alpha$-pregnane anaesthetics which are water soluble may be formulated for injection in a sterile aqueous medium in the absence of a surface active agent.

The anaesthetic solutions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.25 to 3.5 mg/Kg will in general be found to be satisfactory to induce anaesthesia, the preferred dose being within the range of from 0.4 to 2.0 mg/Kg. Generally a dose of about 1.0 mg/Kg is very satisfactory. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of 0.09–1.8 mg/Kg/Min.

Where the anaesthetic solutions are administered intramuscularly, higher doses are generally necessary.

According to a further feature of the present invention there is provided a process for the preparation of $3\alpha$-hydroxy steroids of the pregnane and 19-norpregnane series possessing hydrogen atoms in the $5\alpha$- and $17\alpha$-positions; two hydrogen atoms or an oxo group in the 11-position; an oxo group in the 20-position; and a substituent R (which is an acyloxy, ether, thioether, alkyl, cycloalkyl, aryl, aralkyl, hydroxy, thiocyanato, nitro-oxy or halo substituent) in the $2\beta$-position and $3\alpha$-esters thereof (with the exception of $2\alpha$-thiocyanato-$3\alpha$-hydroxy-$5\alpha$-pregnane-20-one) which comprises reacting a $2\alpha,3\alpha$-epoxide of the pregnane or 19-norpregnane series possessing hydrogen atoms in the $5\alpha$- and $17\alpha$-positions; two hydrogen atoms or an oxo group in the 11-position; an oxo group in the 20-position and, if desired, a 16,17-double bond with a compound of formula RH or with a reaction system producing $R^-$ and a cation followed, where the initial product carries a $3\alpha$ -hydroxy group in deprotonated form, by treatment with a source of protons to form the desired free $3\alpha$-hydroxy group, and where an ester of the $3\alpha$-hydroxy steroid initially produced is desried, by subsequent acylation thereof; where a $\Delta^{16}$ -steroid is produced, this product being subjected to hydrogenation of the 16,17-double bond.

The preparation of compounds having a $2\beta$-halo substituted is conveniently effected by reaction of the $2\alpha,3\alpha$-epoxide with an aqueous solution, preferably concentrated, of a halogen hydracid. This reaction may also be carried out in a two-phase system, the steroid epoxide being dissolved in a water-immiscible organic solvent e.g. methylene chloride or chloroform. In another modification of this reaction the steroid starting material may be reacted with the hydracid in an organic solvent under substantially anhydrous conditions.

Suitable solvents for this last-mentioned reaction include methylene chloride, chloroform, ether and dioxan.

For the preparation of 2β-fluoro compounds it may be convenient to react the epoxy compound under anhydrous conditions in solution with hydrogen fluoride or a complex thereof with a carbamic or thio carbamic acid or esters or amides thereof, e.g. urea. Solvents which are convenient for this reaction include tetrahydrofuran, dimethylformamide, halogenated hydrocarbons e.g. chloroform, or the hydrogen fluoride complex itself e.g. the hydrogen fluoride-urea complex.

The general use of hydrogen fluoride complexes as above referred to for the production of steroid fluorohydrins is described in Canadian Pat. No. 690333.

The reaction of the steroid epoxide with a halogen hydracid may be effected at various temperatures e.g. at from −10° to 100°C, for example, at ambient temperature e.g. 20°C.

The 2β-halo compounds, particularly the 2β-chloro and 2β-bromo compounds may also be prepared by reacting an appropriate epoxide with an appropriate halo-ethanol. The reaction is conveniently effected in the presence of an acid catalyst, for example sulphuric acid. Some 2β-chloroethoxy steroid will be formed simultaneously when chloroethanol is used, as is indicated hereinafter.

The above-defined 2β-substituted 3α-hydroxy-5α-pregnanes having an ether substituent in the 2β-position may be prepared, for example by reacting a corresponding 2α,3α-epoxy-5α-pregnane with an anhydrous alcohol, the alcohol being chosen to provide the desired 2β-substituent.

Where a chloroalkoxy derivative is required the 2α,3α-epoxide may be reacted with a chloroalkanol although as indicated above some 2β-chloro derivative is usually formed simultaneously when chloroethanol is used. 2β-Chloroalkoxy derivatives of this type ca be used to prepare corresponding 2β-aminoalkoxy derivatives by reaction with ammonia or primary or secondary amines, which may be cyclic or acyclic, e.g. morpholine. The replacement of chlorine takes place only with difficulty, for example by heating at 100°C for 24 hours, and it is advantageous first to protect the 20-keto group by ketal formation. The ketal group can readily be removed subsequently by conventional means such as acid hydrolysis.

In general, the reaction with an alcohol is preferably effected in the presence of an acid or basic catalyst. Suitable catalysts include those known for use in the production of ethers by the opening of epoxide rings with alcohols. The reaction is preferably catalysed using an acid catalyst, for example, sulphuric, perchloric and oxalic acid, aluminium chloride and boron trifluoride. Basic catalysts which may be used include alkali-metal alcholates derived from the alcohol used in the reaction. Under such basic conditions the 3α-hydroxy group in the initial product may be partly in deprotonated form and may require regeneration by addition of a source of protons. The reaction will normally be carried out in an excess of the reactant alcohol as solvent but if desired, an aprotic solvent may be present, e.g. an ether solvent such as diethylether or tetrahydrofuran, a hydrocarbon e.g. benzene or a halogenated hydrocarbon e.g. chloroform or methylene chloride. The reaction is preferably effected at about ambient temperature although elevated temperatures, for example at about 50°C may, if desired, be used.

In order to form 2β-(esterified carboxy-alkoxy)-3α-hydroxy steroids, a 2α,3α-epoxide may be reacted with a cyanoalkanol to form a 2β-cyanoalkoxy derivative which may then be treated with an alcohol under acid conditions to form an iminoether salt which on hydrolysis yields the desired ester.

The preparation of 2β-acyloxy substituted 5α-pregnane anaesthetics is preferably effected by reacting the corresponding 2α,3α-epoxy-5α-pregnane with a carboxylic acid. In general, the acid reactant acts as a catalyst for the acylation reaction and where liquid at the reaction temperature, an excess thereof may be used as a solvent for the reaction. However, other solvents may be used, for example the solvents referred to above in relation to 2β-ethers. The reaction is preferably effected at elevated temperatures.

It is particularly useful to react the 2α,3α-epoxide with a chloroalkanoic acid, particularly chloroacetic acid, to yield the corresponding 2β-chloroalkanoyloxy derivative. In the case of chloroacetic acid, it was found preferable where a 3α-hydroxy steroid was required to carry out the reaction in benzene at moderate temperatures e.g. 50°C since higher temperatures e.g. refluxing, gave a significant proportion of 2β,3α-dichloroacetoxy ester. The 2β-chloroalkanoyloxy compounds can be subjected to halogen exchange, e.g. to form 2β-iodoalkanoyloxy derivatives which can then be reacted with primary or secondary amines to give 2β-aminoalkanoyloxy derivatives.

Certain 2β-δ(α-halocycloxy)butoxy compounds according to the invention, particularly 2β-chloroacetoxybutoxy compounds, may be prepared by reaction of the corresponding 2α,3α-epoxide with an appropriate α-halo-carboxylic acid in the presence of tetrahydrofuran, the latter entering into the reaction. In general the δ-(α-haloacyloxy)-butoxy product will predominate but some 2β-(α-haloacyloxy)steroid will also be formed.

Thus, for example, in one experiment when a 2α,3α-epoxide reacted with chloroacetic acid in tetrahydrofuran, the products included 20% of 2β-chloroacetoxy steroid and 60% of 2β-(δ-chloroacetoxy)-butoxy steroid. The reaction may generally be effected under conditions suitable for the preparation of 2β-acyloxy compounds as hereinbefore set forth. 2β-δ(α-Haloacyloxy)butoxy steroids can be subjected to hydrolysis to yield the corresponding 2β-δ-hydroxy-n-butoxy-steroids. 2β-(δ-Chloroacyloxy)butoxy steroids may be subjected to halogen exchange to form, for example, the corresponding iodoacyloxybutoxy steroid which may then be reacted with ammonia or a primary or secondary amine to yield a corresponding aminoacyloxy-butoxy steroid.

Steroids having a thioether group in the 2β-position can be prepared by reacting the 2α,3α-epoxide with a corresponding thiol, preferably in the presence of an acid catalyst, e.g. a Lewis acid such as BF$_3$, conveniently in the form of its etherate. The reaction is conveniently effected in an ether solvent.

2β-Acylthio steroids can be formed by reaction of a thiocarboxylic acid with the 2α,3α-epoxide. An acid catalyst is preferably present, for example a Lewis acid such as BF$_3$, conveniently in the form of an etherate. The reaction is conveniently effected in an ether solvent.

2β-Nitro-oxy-3α-hydroxy-5α-pregnanes may be prepared by the reaction of the corresponding 2α,3α-epoxides with concentrated nitric acid in an organic solvent. Suitable solvents include etheric solvents e.g.

diethyl ether, dioxan, tetrahydrofuran, diglyme, ethyleneglycol monomethyl ether. The reaction may for example be effected at ambient temperature.

2β-Thiocyanato-3α-hydroxy-5α-pregnanes may be prepared by reaction of the corresponding 2α, 3α-epoxides with thiocyanic acid oranalkali metal (e.g. sodium or potassium) thiocyanate or ammonium thiocyanate, conveniently in an etheric solvent for example of the type referred to in the last-preceding paragraph, in the presence of an acid catalyst e.g. perchloric acid when using thiocyanates. The reaction may, for example, be effected at ambient temperature.

2β-Alkyl, cycloalkyl, aryl or aralkyl-3α-hydroxy-5α-pregnanes may be readily prepared from the corresponding 2α,3α-epoxides by reaction with a lithium di-(alkyl, cycloalkyl, aryl or aralkyl) cuprate conveniently in an etheric solvent e.g. diethyl ether or a hydrocarbon solvent e.g. hexane. The reaction may be effected in known manner for example as described by Herr et al (J.A.C.S. 1970, 92, 3813). The 2β-substituted steroid initially formed has at the 3α-position an O-metal substituent which is subsequently converted to OH by treatment with a source of protons such as aqueous ammonium chloride.

3α-Acyloxy esters of the 3α-hydroxy-2β-substituted-pregnane anaesthetics may be prepared from the corresponding 3α-hydroxy compounds by acylation in known manner. This acylation may for example be effected using a reactive derivative of the carboxylic acid such as an anhydride or acid halide. In general, the acylation is preferably effected in an aprotic solvent, for example, a halogenated hydrocarbon e.g. chloroform or methylene chloride. The acylation is preferably effected in the presence of an acid binding agent such as a tertiary organic base, for example, pyridine.

2β,3α-Dihydroxy-5α-pregnanes may be prepared, for example, by hydrolysis of the corresponding 2α,3α-epoxy-5α-pregnane. This hydrolysis is generally effected in an aqueous medium, preferably containing a water miscible aprotic organic solvent such as acetone or tetrahydrofuran generally to aid the solubility of the steroid. The hydrolysis is advantageously effected under acidic conditions, for example, using an aqueous solution of an inorganic acid e.g. perchloric or sulphuric acid.

Compounds according to the invention wherein R represents an azido group may be prepared, for example, by reacting a corresponding 2α,3α-epoxy steroid with an alkali metal azide e.g. sodium azide, in the presence of a source of protons. The reaction may conveniently be effected in a solvent, for example dimethyl sulphoxide or dimethyl formamide. Suitable proton sources comprise mineral acids such as sulphuric acid and boric acid. The reaction is preferably effected at an elevated temperature.

2β-Azido compounds according to the invention may also be prepared by reacting a corresponding 2β-tosyloxy compound with an alkali metal azide e.g. sodium azide conveniently in a solvent such as dimethylsulphoxide. The reaction is preferably effected at an elevated temperature. Such a tosyloxy derivative can be prepared by reaction of the 2α,3α-epoxide with substantially anhydrous p-toluene sulphonic acid.

As above-mentioned, the introduction of the desired substituent by suitable reaction with a 2α,3α-epoxide may be effected upon a $\Delta^{16}$ compound, the double bond thereafter being reduced to produce the desired saturated ring structure, the introduction of the desired 2β-substituent being effected by the methods described above for the corresponding saturated compounds. Reduction of the $\Delta^{16}$-double bond is conveniently effected by hydrogenation preferably in an organic solvent, for example methanol, ethanol, propanol, diethylether, tetrahydrofuran, chloroform, methylene chloride or ethyl acetate. As hydrogenation catalyst, palladium catalysts for example palladised charcoal, Raney nickel and platinum catalysts may be used. The hydrogenation is further preferably effected in the presence of a tertiary base e.g. triethylamine.

In hydrogenating the above-described 5α-pregn-16-enes, conditions should be chosen to avoid reducing substituents already present in the molecule.

Compounds according to the invention having a 16-position alkyl group may be prepared by known methods. 16α-Alkyl compounds may be also prepared by reacting a corresponding $\Delta^{16}$-steroid with an appropriate lithium dialkyl, cuprate, preferably in the presence of an etheric solvent, e.g. diethyl ether. This reaction may, if desired, be effected simultaneously with the introduction of a 2β-alkyl group as hereinbefore described, that is by reacting a 2α,3α-epoxy-20-keto-5α-pregn-16-ene with the lithium dialkyl cuprate reagent.

5α-pregn-16-enes are also useful intermediates for the preparation of compounds having a substituent at position 16, for example, chloro, and alkoxy substituents. Such substituents may be introduced in known manner.

21-Acyloxy substituents may be introduced into the above-defined 2β-substituted-3α-hydroxy 5α-pregnane compounds or into intermediates used in their production by known methods. Such methods include acyloxylation, and especially acetoxylation of the corresponding 21-unsubstituted compound with a lead tetraacylate preferably in the presence of a Lewis acid. The 3α-hydroxy group of the starting compounds may if necessary be protected in known manner.

21-Acyloxy compounds may also be prepared in known manner via the corresponding 21-chloro, 21-bromo or 21-iodo compounds as described in our Belgian Pat. No. 752165.

Compounds according to the invention having a 3α-amino or substituted aminoalkanoyloxy group may be prepared for example from the corresponding 3α-haloalkanoyloxy compounds by reaction with ammonia or an appropriate amine. The reaction may conveniently be effected in a solvent for example a halogenated hydrocarbon e.g. methylene chloride.

Compounds according to the invention having a basic centre, for example 2β-aminoalkoxy or alkanoyloxy or 3α-aminoalkanoyloxy compounds may, if desired, be converted into acid addition salts thereof. Known methods may be used to prepare such salts which may be with inorganic acids (e.g. hydrochloric acid, sulphuric acid or phosphoric acid) or organic acids (e.g. acetic acid, propionic acid, citric acid, maleic acid, methane sulphonic acid or tartaric acid).

The following Examples are given by way of illustration only. All temperatures are in degrees Celsius. All optical rotations were determined for solutions in chloroform (1% w/v unless otherwise stated) at room temperature. Preparative thin layer chromatography (preparative tlc) was carried out using plates coated with a 2mm layer of silica fluorescing at 254 and 366mμ. Petrol refers to petroleum ether (b.p. 60°–80°).

Example 1

2β-Fluoro-3α-hydroxy-5α-pregnane-11,20-dione.

Anhydrous hydrofluoric acid (50 ml.) was added slowly to urea (40 g.) to give a colourless liquid. To 11 ml. of the liquid was added 2α,3α-epoxy-5α-pregnane-11,20-dione (650 mg.), and the clear solution was stirred at room temperature overnight. It was poured into saturated sodium bicarbonate solution (250 ml), and the white precipitate was extracted into chloroform. The organic solution was washed with water, dried over sodium sulphate and evaporated to give a white foam (565 mg.). Recrystallisation from acetonepetrol gave the title compound m.p. 174°–178°, $[\alpha]_D$ $\alpha+_{114}°$.

Examples 2–29

Various compounds according to the invention were prepared according to methods A-D below the amounts of various reactants and details of the products being set out in the following Tables.

Method A Preparation of 2β-halo-3α-hydroxy-5α-pregnanes

The 2α,3α-epoxy-5α-pregnane was dissolved in chloroform and the solution was treated with the appropriate hydrohalic acid. The mixture was stirred vigorously for approximately one-half hour at room temperature and then poured into chloroform. The organic solution was washed with water, then dilute sodium bicarbonate solution, then again with water, dried over sodium sulphate, and evaporated to give a crystalline residue which was purified by recrystallisation.

Method B

Preparation of 2β-alkoxy-3α-hydroxy-5α-pregnanes

The 2α,3α-epoxy-5α-pregnane was dissolved in the appropriate alcohol, and concentrated sulphuric acid (catalyst) was added. The solution was stirred for approximately one-half hour., and then poured into water, to give a white crystalline precipitate which was filtered off and dried in vacuo over phosphorus pentoxide to give the product.

Method C

Preparation of 2β-alkoxy-3α-hydroxy-5α-pregnanes

The 2α,3α-epoxy-5α-pregnane in ether was treated with the appropriate alcohol. Boron trifluoride etherate was added to the solution and the mixture was stirred at room temperature for 1 hour. The solution was neutralised with sodium bicarbonate solution. The organic layer was washed with water and dried over anhydrous sodium sulphate. Evaporation of the solvent gave the crude product which was purified by preparative thin layer chromatography in ethyl acetate/petroleum ether.

Method D

Preparation of 2β-alkoxy(halo)-3α-hydroxy-5α-pregnanes

The 2β-substituted-3α-hydroxy-5α-pregn-16-ene in ethyl acetate and triethylamine was hydrogenated over 5% palladium-on-charcoal catalyst at atmospheric pressure for 30 minutes. The catalyst was filtered off and the filtrate ws evaporated to a white solid. Recrystallisation gave the crystalline product.

Et OAc = Ethyl Acetate
trit = triturated.

General Formula

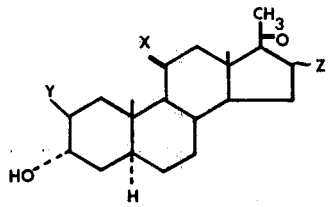

d = decomposition

| Ex. No. | Z | X | Y | Method of Preparation | Weight of epoxide (mg) | Amount of reagent HY(ml) | Amount of solvent (ml) | Crystallisation solvent | Yield (mg) | M. pt. (°C) | $[\alpha]_D$ | Amount of Catalyst (ml.) |
|---|---|---|---|---|---|---|---|---|---|---|---|---|
| 2 | H | =O | Cl | A[1] | 682 | 15[9] | 25 | EtOAc | 413 | 185–189 | +117 | — |
| 3 | H | =O | Br | A | 502 | 10[9] | 30 | acetone/ether | 483 | 206–210 | +106 | — |
| 4 | H | =O | I | A[2] | 600 | 5[9] | 25 | EtOAc/petrol | 395 | 108–109 (d) | +109 | — |
| 5 | H | —H₂ | Cl | A | 303 | 6[9] | 10 | EtOAc | 137 | 175–179 | +105 | — |
| 6 | H | —H₂ | Br | A | 356 | 7[9] | 20 | EtOAc/ether | 144 | 171–175 | +117 | — |
| 7 | H | =O | CH₃O— | B | 200 | 20 | — | — | 175 | 163–164 | +109 | 0.1 |
| 8 | H | =O | C₂H₅O— | B[8] | 500 | 30 | — | — | 340 | 74–78 | +100 | 0.15 |
| 9 | H | =O | iC₃H₇O— | B[3,4] | 500 | 25 | — | acetone/petrol | 300 | 154–158 | +103.5 | 0.5 |
| 10 | H | =O | ClC₂H₄O— | B[4] | 500 | 25 | — | — | 360 | — | +87.5 | 0.5 |
| 11 | H | —H₂ | CH₃O— | B | 500 | 25 | — | — | 385 | 176–179 | +102 | 0.1 |
| 12 | H | —H₂ | C₂H₅O— | B | 1.4g | 90 | — | ether/petrol | 1.44g | 114–121 | +84* | 0.42 |
| 13 | H | =O | nC₃H₇O— | B[3,4,8] | 2.0g | 60 | — | acetone/petrol | 1.24g | 108–110 | +96 | 0.5 |
| 14 | H | =O | CH₃OC₂H₄O— | B[3,4] | 2.0g | 50 | — | — | 1.41g | — | +95.5 | 0.5 |
| 15 | H | =O | —O—⟨⟩ | B[4] | 519 | 25 | — | — | 188 | — | +98 | 0.5 |
| 16 | H | =O | tC₄H₉O— | B[3,4] | 1.0g | 50 | — | ether/ | 90 | 196–202 | — | 0.25 |

-continued

General Formula

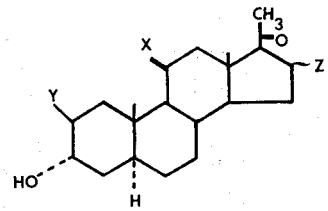

d = decomposition

| Ex. No. | Z | X | Y | Method of Preparation | Weight of epoxide (mg) | Amount of reagent HY(ml) | Amount of solvent (ml) | Crystallisation solvent | Yield (mg) | M. pt. (°C) | $[a]_D$ | Amount of Catalyst (ml.) |
|---|---|---|---|---|---|---|---|---|---|---|---|---|
| 17 | H | =O | ⌬CH₂O- | B[3,5] | 1.0g | 30 | — | petrol trit aq.acetone | 430 | 165–171 | +83.5 | 0.3 |
| 18 | H | =O | CH₂=CHCH₂O— | B[4] | 660 | 4 | 6 | — | 316 | — | +59.5 | 3 drops |
| 19 | αMe | =O | Cl | A | 200 | 7 | 8 | EtOAc/petrol | 130 | 216–224 | +99° | — |
| 20 | αMe | =O | MeO— | B[3,5] | 200 | 10 | — | EtOAc/petrol | 160 | 206–210 | +97.5 | 0.05 |
| 21 | H | =O | 2-Cl(CH₂)₂O— | C | 330 | 5 | 25 | — | 310 | — | +87.5 | 5 drops |
| 22 | H | =O | nC₄H₉O— | C[6] | 500 | 2 | 100 | — | 480 | — | +99° | 10 drops |
| 23 | H | =O | C₆H₅O- | C[7,4] | 1.0g | 6g. | — | acetone/petrol | 325 | 229–231 | +79.2 | 1.0 ml. |
| 24 | H | =O | C₆H₅CH₂O- | B[5] | 500 | 5 | — | acetone | 225 | 197–202 | +91.3 | 0.2 |
| 25 | H | =O | Cl(CH₂)₃O— | C | 1.0g | 5 | 50 | — | 680 | — | +82.7 | 10 drops |

NOTES
[1]Product was purified by preparative thin layer chromatography on silica gel in chloroform before recrystallisation.
[2]The organic solution was washed with sodium bisulphite instead of sodium bicarbonate.
[3] The reaction mixture was diluted with potassium bicarbonate (10%) before dilution with water.
[4]The product was extracted with ether and the extract washed with water and dried over sodium sulphate. Evaporation of the ether gave a product which was purified by preparative TLC on silica in ethyl acetate/petrol.
[5]The product was extracted with ether.
[6]After 1 hour, the reaction was incomplete and a further portion of BF₃ etherate was added.
[7]The solution was neutralised with potassium hydroxide instead of sodium bicarbonate.
[8]The solution was heated gently to keep the steroid in solution.
[9]The acids used in the reaction were of the following strength: HCl concentrated, HI 55%, and HBr 48%.

Compounds prepared by Method D

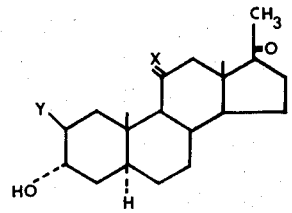

| Ex. No. | Y | X | Weight of starting material(mg) | Amount of EtOAc(ml) | NEt₃(ml.) | Catalyst (mg) | Crystallisation solvent | Yield (mg) | M. pt (°C) | $[\alpha]_D$ |
|---|---|---|---|---|---|---|---|---|---|---|
| 26 | Cl | =H₂ | 50 | 5 | 0.1 | 10 | EtOAc/petrol | 36 | 178–183 | +105 |
| 27 | CH₃O— | =H₂ | 50 | 10 | 0.1 | 10 | EtOAc/petrol | 42 | 178–180 | +102 |
| 28 | Cl | =O | 65 | 20 | 0.15 | 15 | EtOAc | 55 | 189–193 | +117 |
| 29 | CH₃O— | =O | 150 | 35 | 0.2 | 20 | EtOAc/petrol | 135 | 161–163 | +108 |

Et OAc = Ethyl Acetate
trit = triturated.

Example 30

3α-Hydroxy-2β-methoxy-5α-pregnane-11,20-dione a In a series of reactions, 2α,3α-epoxy-5α-pregnane-11,20-dione (100 mg. 0.3 m.mole) was reacted at ambient temperature with methanol (5 ml) in the presence of a variety of catalysts. The catalyst used, the amount thereof and the reaction time are given for each case in the following table. With the exception of the reaction catalysed by $AlCl_3$, the reaction mixture was neutralised with potassium bicarbonate solution after the time given in the table. Water was then added to the neutralised reaction mixture and the precipitated title compound was filtered off and dried in vacuo over phosphorus pentoxide.

The $AlCl_3$ catalysed reaction mixture was diluted with dilute aqueous hydrochloric acid and the resulting solution was extracted with chloroform, the extract was evaporated and the crude product was recrystallised to give the title compound.

Reaction of 2α,3α-epoxy-5α-pregnane-11,20-dione with methanol in the presence of various catalysts

| Reaction No. | Catalyst | Amount | Molar Eq. | Reaction Time | Isolated Yield % |
|---|---|---|---|---|---|
| 1 | $H_2SO_4$ (conc.) | 0.01 ml | 0.6 | 10 min | 57 |
| 2 | $H_2SO_4$ (conc.) | 0.1 ml | 6 | 5 min | 64 |
| 3 | $H_2SO_4$(2N) | 0.1 ml | 0.3 | 1 hr | 56 |
| 4 | $HClO_4$ (70%) | 0.01 ml | 0.3 | 20 min | 61 |
| 5 | HCl(conc.) | 0.01 ml | 0.4 | 20 min | 68 |
| 6 | $P_2O_5$ | 15 mg | 0.3 | 25 min | 60 |
| 7 | $(CO_2H)_2$ $2H_2O$ | 40 mg | 1 | 72 hr | 76 |
| 8 | $TsOH.H_2O$ | 55 mg | 1 | 10 min | 70 |
| 9 | $BF_3.Et_2O$ | 0.01 ml | 0.6 | 45 min | 71.5 |
| 10 | $AlCl_3$ | 40 mg | 1 | 40 min | 70 |
| 11 | $SOCl_2$ | 0.025 ml | 1 | 10 min | 69 |
| 12 | $POCl_3$ | 0.01 ml | 0.4 | 10 min | 63 |
| 13 | $Me_2SO_4$ | 0.015 ml | 0.5 | 2.5 hr | 69 |
| 14 | $CH_3COCl$ | 0.01 ml | 0.5 | 10 min | 73 |

(b) The reaction of 2α,3α-epoxy-5α-pregnane-11,20-dione with sodium methoxide

Sodium (70 mg.) was dissolved in dry methanol (5 ml.), and to the resulting solution of sodium methoxide (about 166 mg,) was added 2α,3α-epoxy-5α-pregnane-11,20-dione (100 mg). The solution was refluxed for 5 days, then water was added, and the mixture was neutralised with dilute hydrochloric acid and extracted into chloroform. The extract was dried over sodium sulphate and evaporated to a brown oil which was purified by preparative TLC in ethyl acetate/petrol (1/1). The title compound was recrystallised from ethyl acetate/petrol (21 mg).

Example 31

3α-Hydroxy-2β-methyl-5α-pregnane-11,20-dione

A 1.6 molar solution of methyl lithium in ether (30 ml.) was added to a stirred suspension of cuprous iodide (4.56 g.) in dry ether (100 ml.) under nitrogen at −20°. A cold solution of 2α,3α-epoxy-5α-pregnane-11,20-dione (1.33 g.) in dry ether (20 ml.) was then added and the mixture was maintained at 0° for 40 hours and then at room temperature for 4 hours. The mixture was then poured into aqueous ammonium chloride solution and extracted into ethyl acetate. The organic extract was washed with water, dried ($MgSO_4$) and evaporated in vacuo. The residue (2.9 g.) was purified by preparative TLC and crystallisation from methyl acetate/petroleum ether to give the title compound (0.5 g.) m.p. 142°–146° $[\alpha]_D$ + 121+ (c 0.8).

Example 32

21-Bromo-3α-hydroxy-2β-methoxy-5α-pregnane-11,20-dione

A solution of 3α-hydroxy-2β-methoxy-5α-pregnane-11,20-dione (2g.) in methanol (15 ml.) was treated with hydrobromic acid in glacial acetic acid (3 drops). The mixture was stirred at room temperature and bromine (530 mg.) in methanol (1.45 ml.) was added dropwise over a period of 30 minutes. The mixture was stirred for a further 30 minutes and poured into water, stirred, filtered, washed with water and dried. Purification by preparative tlc, followed by crystallisation from ethyl acetate and petrol gave the title compound (250mg) as colourless plates; m.p. 185°–188° $[\alpha]_D$ + 104°.

Example 33

21-Acetoxy-3α-hydroxy-2β-methoxy-5α-pregnane-11,20-dione.

21-Bromo-3α-hydroxy-2β-methoxy-5α-pregnane-11,20-dione (600 mg.) was dissolved in dry acetone (15 ml.) and added to a mixture of glacial acetic acid (2 ml.) and triethylamine (3ml.) and refluxed for 4½ hours. The mixture was diluted with chloroform, washed with water, dried and evaporated to a foam. Purification by preparative tlc followed by crystallisation from ethyl acetate and petrol gave the title compound (230 mg.) as colourless plates; m.p. 177°–180° $[\alpha]_D$ + 112°.

Example 34

2β,3α-Dihydroxy-5α-pregnane-11,20-dione

2α,3α-Epoxy-5α-pregnane-11,20-dione (207 mg.) in hot tetrahydrofuran (6 ml.) was treated with perchloric acid (60%, 0.05 ml.) in tetrahydrofuran (2 ml.) and water (2 ml.). The reaction mixture was concentrated to 5 ml., allowed to stand for 15 minutes and boiled for 30 minutes with the concurrent addition of water. The mixture was poured into ethyl acetate, and the aqueous layer was extracted with ethyl acetate. The combined organic extract was washed with water, dried over sodium sulphate and evaporated to a crystalline mass which was purified by preparative TLC to give the title compound (70 mg.) as colourless crystals, m.p. 194°–198°, $[\alpha]_D$ + 103.5°.

Example 35

3αHydroxy-2β-thiocyanato-5α-pregnane-11,20-dione

2α,3α-Epoxy-5α-pregnane-11,20-dione (500 mg.) and potassium thiocyanate (2 g.) in dry tetrahydrofuran (40 ml.) were treated with tetraphosphoric acid (about 2 ml.), and the reaction was stirred at room temperature for 2 hours. Perchloric acid (60%, 0.1 ml.) was added, and after a further 30 minutes the solution was diluted with water and extracted with ether. The extract was washed with water, dried over sodium sulphate and evaporated to give a colourless oil which was purified by preparative tlc and recrystallisation from acetone/petrol to give the title compound, as white prisms m.p. 165°–170° $[\alpha]_D$ + 78°.

Example 36

2β,3α-Dihydroxy-5α-pregnane-11,20-dione 2-nitrate

2α,3α-Epoxy-5α-pregnane-11,20-dione (1.0 g.) was dissolved in ether (50 ml.) and to the stirred solution was cautiously added fuming nitric acid (0.5 ml.). The solution was stirred at room temperature overnight and then poured into ether (100 ml.) and water (100 ml.). The ether layer was washed with water, dilute potassium bicarbonate solution, and water, dried over sodium sulphate and evaporated to a yellow oil (1.24 g.). The product was purified by preparative tlc to give the title compound as a white solid, m.p. 170°–176°, $[\alpha]_D$ + 74°.

Example 37

3α-Acetoxy-2β-ethoxy-5α-pregnane-11,20-dione

2β-Ethoxy-3α-hydroxy-5α-pregnane-11,20-dione (500 mg.) in dry methylene chloride (5 ml.) at 0° was treated with pyridine (2.0 ml.) and acetic anhydride (2.0 ml.). After 24 hours, methylene chloride was added, and the solution was washed with dilute hydrochloric acid and with water. It was then dried over sodium sulphate and evaporated to an oil. The title compound (350 mg.) was obtained as a colourless foam, $[\alpha]_D$ + 132°.

Example 38

2β-Ethoxy-3α-propionyloxy-5α-pregnane-11,20-dione

2β-Ethoxy-3α-hydroxy-5α-pregnane-11,20-dione (500 mg.) in pyridine (2.5 ml.) was treated with propionic anhydride (2.5 ml.), and the solution was left at room temperature overnight. Water was added, and the mixture was extracted with chloroform. The extract was washed with dilute hyrochloric acid, dried over sodium sulphate and evaporated to an oil which was purified by preparative tlc to give the title compound (295 mg.) as a colourless foam $[\alpha]_D$ + 107°.

Example 39

2β-Methoxy-3α-trifluoroacetoxy-5α-pregnane-11,20-dione

A solution of 3α-hydroxy-2β-methoxy-5α-pregnane-11,20-dione (500 mg.) in methylene chloride (20 ml.) was treated with a solution of trifluoroacetic anhydride (0.6 ml.) in methylene chloride (10 ml.) at 0°. The mixture was allowed to warm to room temperature and stirred for 2½ hours. The solution was diluted with methylene chloride, washed with water, saturated sodium bicarbonate solution and again with water, dried and evaporated to a foam. Purification by tlc gave the title compound (440 mg.) $[\alpha]_D$ + 109°.

Example 40

3α-Acetoxy-2β-bromo-5α-pregnane-11,20-dione

2β-Bromo-3α-hydroxy-5α-pregnane-11,20-dione (750 mg.) in pyridine (2 ml.) was treated with acetic anhydride (1 ml.) and the mixture was allowed to stand at room temperature overnight. It was then poured into water to give a white solid (720 mg.) which was recrystallised from methanol to give the title compound (471 mg.) as white crystals, m.p. 154°–156°, $[\alpha]_D$ + 128.5°.

Example 41

2β,16α-Dichloro-3α-hydroxy-5α-pregnane-11,20-dione

2α,3α-Epoxy-5α-pregn-16-ene-11,20-dione (600 mg.) in chloroform (25 ml.) was shaken with concentrated hydrochloric acid (25 ml.) for 2 hours. The organic layer was washed with water, dried over sodium sulphate and evaporated to an oil which was purified by preparative tlc to give 2β-chloro-3α-hydroxy-5α-pregn-16-ene-11,20-dione as the major product. Also isolated was the title compound (75 mg.) as fine white crystals, m.p. 192°–194°, $[\alpha]_D$ + 98°.

Example 42

2β,16α-Dichloro-3α-hydroxy-5α-pregnane-11,20-dione

2α,3α-Epoxy-5α-pregn-16-ene-11,20-dione (660 mg.) was dissolved in dioxan (40 ml.) and the solution was saturated with dry hydrogen chloride. After 2 hours, the solution was poured into water and the precipitate extracted into chloroform. The extract was washed with water until the washings were neutral, dried over sodium sulphate and evaporated to a foam which was purified by preparative tlc and recrystallisation from ethylacetate/petrol to give the title compound (426 mg.) as colourless needles, m.p. 192°–196°, $[\alpha]_D$ + 98°.

Example 43

Reaction of 2α,3α-Epoxy-5α-pregnane-11,20-dione with Chloroacetic Acid in Tetrahydrofuran.

Chloroacetic acid (8 g.) was dissolved in dry tetrahydrofuran (8 ml.) at 50°–55° and to the stirred solution was added 2α,3α-epoxy-5α-pregnane-11,20-dione (1.0 g.). The reaction solution was stirred at 50° for 4 hours. The reaction mixture was diluted with icecold water (50 ml.) and extracted with chloroform (2 × 50 ml.). The extract was washed with dilute potassium bicarbonate solution and with water, dried over sodium sulphate and evaporated to an oil (about 1.3 g.) which was purified by preparative tlc on 120 g. of silica in ethyl acetate/petroleum ether 1/1, run three times, the two closely running major bands being separated. The upper band ($R_F$ 0.35 – 0.45) yielded 2β-chloroacetoxy-3α-hydroxy-5α-pregnane-11,20-dione (307 mg.) as a white foam, $[\alpha]_D$ + 79.0° (c 0.85).

The lower band from the tlc plates ($R_F$ 0.15 – 0.35) yielded 2β-(4'-chloroacetoxy-n-butoxy)-3α-hydroxy-5α-pregnane-11,20-dione (735 mg.) as an unstable foam which collapsed to a gum on standing, $[\alpha]_D$ + 69.0° (c 0.68).

Example 44

2β-Chloroacetoxy-3α-hydroxy-5α-pregnane-11,20-dione a. A solution of chloroacetic acid (5 g.) in benzene (40 ml.) was refluxed under a Dean and Stark head for 15 minutes. 2α,3α-Epoxy-5α-pregnane-11,20-dione (1 g.) was added and reflux continued for a further 2 hours. Ether (40 ml.) was added to the cooled solution and the organic mixture washed with sodium bicarbonate solution until effervescence had ceased. The organic layer was washed with water (2 × 100 ml.), dried over anhydrous sodium sulphate and evaporated in vacuo to a pale yellow foam (1.29 g.) which was chromatographed on a silica (50 g.) column using chloroform as eluant. Fractions 4–12 (50 ml. each) gave the title compound (500 mg.) as a white foam.

Fractions 1 and 2 were purified by preparative tlc using chloroform/ethyl acetate 1/1 to give 2β,3α-di-(-chloroacetoxy)-5α-pregnane-11,20-dione (330 mg.) as a white foam, $[\alpha]_D + 91.5°$. (b) Similarly, using the same amounts of the various reagents as in (a) above with the reaction mixture maintained at a temperature of 50° for 5 hours and after isolation as in (a) above gave the title compound (900 mg.).

Example 45

3α-Hydroxy-2β-iodoacetoxy-5α-pregnane-11,20-dione

2β-Chloroacetoxy-3α-hydroxy-5α-pregnane-11,20-dione (300 mg.) was dissolved in acetone (30 ml.). Sodium iodide (310 mg.) was added and the mixture refluxed for 40 minutes, a crystalline solid precipitating in this time. The solid was filtered off and the filtrate evaporated to a pale green solid which was partitioned between ether/water. The organic layer was dried over anhydrous sodium sulphate and evaporated in vacuo to give the title compound as an off-white foam (325 mg.) $[\alpha]_D + 67°$ (c 1.01).

Example 46

2β-N,N-Diethylaminoacetoxy-3α-hydroxy-5α-pregnane-11,20-dione

3α-Hydroxy-2β-iodoacetoxy-5α-pregnane-11,20 dione (385 mg.) was dissolved in dried methylene chloride (30 ml.) and diethylamine (1 ml.) added to the stirred solution. The mixture was stirred at room temperature for 40 minutes. Methylene chloride (50 ml.) was added and the mixture was washed with water (100 ml.), dried over anhydrous sodium sulphate and evaporated to an orange oil (345 mg.) which was purified by preparative tlc in acetone to give the title compound (290 mg.) as a white foam. $[\alpha]_D + 72.9°$ (c 0.94).

Example 47

3α-Hydroxy-2β-morpholinoacetoxy-5α-pregnane-11,20-dione

3α-Hydroxy-2β-iodoacetoxy-5α-pregnane-11,20-dione (578 mg.) was dissolved in dried methylene chloride and morpholine (1 ml.) was added to the solution. The mixture was stirred at room temperature for one-half hour, a white precipitate forming. The mixture was filtered and the filtrate evaporated in vacuo to a yellow oil (340 mg.) which was purified by preparative tlc in ethyl acetate run twice to give the title compound (200 mg.) as a white foam. $[\alpha]_D + 65°$ (c 0.48).

Example 48

3α-Hydroxy-2β-piperidinoacetoxy-5α-pregnane-11,20-dione

3α-Hydroxy-2β-iodoacetoxy-5α-pregnane-11,20-dione (550 mg.) was dissolved in methylene chloride (25 ml.) and piperidine (1 ml.) added to the solution. The mixture was stirred at room temperature for 1 hour. The solution was evaporated to a pale yellow solid which was partitioned between ether/water. The organic layer was dried over anhydrous sodium sulphate and evaporated to a white foam (460 mg.) which was purified by preparative tlc in acetone/petroleum ether 1/1. The main band ($R_F$ 0.4 – 0.5) gave the title compound (420 mg.) as a white foam. $[\alpha]_D + 80.4°$ (c 0.99).

Example 49

3α-Hydroxy-2β-(4′-iodoacetoxy-n-butoxy)-5α-pregnane-11,20-dione

2β-(4′-Chloroacetoxy-n-butoxy)-3α-hydroxy-5α-pregnane-11,20-dione (450 mg.) was dissolved in acetone (30 ml.) and sodium iodide (460 mg.) added to this solution. The mixture was refluxed for 1 hour, a white precipitate forming in this time. The mixture was filtered and the filtrate evaporated to a yellowish solid which was partitioned between ether and water. The ethereal solution was dried over anhydrous sodium sulphate and evaporated in vacuo to give the title compound (467 mg.) as a pale yellow foam which almost immediately collapsed to a gun. This unstable product was used immediately for the following Examples 50 and 51

Example 50

3α-Hydroxy-2β-(4′-morpholinoacetoxy-n-butoxy)-5α-pregnane-11,20-dione

3α-Hydroxy-2β-(4′-iodoacetoxy-n-butoxy)-5α-pregnane-11,20-dione (467 mg.) was dissolved in dried methylene chloride (30 ml.) and morpholine (1 ml.) added to this solution. The mixture was stirred at room temperature for 1 hour, a white precipitate forming in this time. The mixture was filtered and the filtrate evaporated to a yellow oil which was purified by preparative tlc in ethyl acetate (run twice) to give the title compound (220 mg.) as a colourless oil. $[\alpha]_D + 57.1°$ (c 0.49).

Example 51

2β-(4′-N,N-Diethylaminoacetoxy-n-butoxy)-3α-hydroxy-5α-pregnane-11,20-dione

3α-Hydroxy-2β-(4′-iodoacetoxy-n-butoxy)-5α-pregnane-11,20-dione (355 mg.) was dissolved in dried methylene chloride (30 ml.) and diethylamine (1.5 ml.) added to the stirred solution. The mixture was stirred at room temperature for 1 hour. Methylene chloride was added and the solution washed with water (2 × 100 ml.), dried over anhydrous sodium sulphate and evaporated to an orange oil (400 mg.) which was purified by preparative tlc in ethyl acetate to give impure title compound (260 mg.).

Example 52

2β-(4′-Hydroxy-n-butoxy)-3α-hydroxy-5α-pregnane-11,20-dione

2β-(4′-Chloroacetoxy-n-butoxy)-3α-hydroxy-5α-pregnane-11,20-dione (380 mg.) was dissolved in methanol (40 ml.) and the stirred solution heated to 50°C. Perchloric acid (0.5 ml.) was added and the mixture stirred at 50°C for 5 hours. The mixture was neutralised with sodium bicarbonate solution, poured into water and extracted with ether (2 × 100 ml.). The combined extracts were washed with water (200 ml.), dried over anhydrous sodium sulphate and evaporated in vacuo to a white foam (270 mg.) which was purified by preparative tlc in acetone/petroleum ether 1/1 to give the title compound (170 mg.) $[\alpha]_D + 79.5°$

Example 53

Reaction of 2α, 3α-epoxy-5α-pregnane-11,20-dione with 2-bromoethanol

2α, 3α-Epoxy-5α-pregnane-11,20-dione (660 mg.) was dissolved in ether (70 ml.) and 2-bromoethanol (1 ml.) added to the solution. Concentrated sulphuric acid (0.5 ml.) was then added and the mixture stirred at room temperature for one-half hour. 10% Potassium bicarbonate solution (18 ml.) was added and when effervescence had ceased the aqueous layer was removed and extracted with ether (20 ml.). The combined organic extracts were washed with water (100 ml.), dried over anhydrous sodium sulphate and evaporated in vacuo to a pale yellow oil (794 mg.) which was purified by preparative tlc. The main band ($R_F \sim 0.3$) gave 2β-bromo-3α-hydroxy-5α-pregnane-11,20-dione (230 mg.), m.p. 172°–3°C identical with a previously prepared sample.

Example 54

2β-(2'-Chloroethoxy)-3α-hydroxy-5α-pregnane-11,20-dione

2α,3α-Epoxy-5α-pregnane-11,20-dione (1 g.) was dissolved in 2-chloroethanol (50 ml.) and concentrated sulphuric acid (6 drops) added to the solution. The mixture was stirred at room temperature for 1 hour, neutralised with sodium bicarbonate solution and poured into water (500 ml.). The precipitate formed was extracted into ether (2 × 100 ml.) and the combined extracts washed with water (2 × 100 ml.). The organic layer was dried over anhydrous sodium sulphate and evaporated to a yellow oil (1.5 g.) which was purified by preparative tlc using ethyl acetatepetroleum ether, 1/1 run 3 times. The main band ($R_F \sim 0.2 - 0.3$) gave the title compound (640 mg.) as an off-white foam identical with a previously prepared sample.

The second major band ($R_F \sim 0.35$) gave 2β-chloro-3α-hydroxy-5α-pregnane-11,20-dione (205 mg.) as a white crystalline solid, m.p. 185°–189°C, identical with an authentic sample.

Example 55

3α-Hydroxy-2β-(2'-morpholinoethoxy)-5α-pregnane-11,20-dione

2β(2'-Chloroethoxy)-3α-hydroxy-5α-pregnane-11,20-dione (100 mg.) was dissolved in morpholine (10 ml.) and the solution heated on a steam-bath for 24 hours, complete reaction occurring. The morpholine was evaporated off in vacuo and the orange oil obtained purified by preparative TLC in ethyl acetate to give the title compound (40 mg.) as a pale yellow oil.

Example 56

2β-(2'-Chloroethoxy)-20,20-ethylenedioxy-3α-hydroxy-5α-pregnan-11-one

2β-(2'-Chloroethoxy)-3α-hydroxy-5α-pregnane-11,20-dione (600 mg.) was dissolved in benzene (50 ml.), ethylene glycol (5 ml.) and toluene-p-sulphonic acid (2 mg.) added, and the vigorously stirred mixture refluxed under a Dean and Stark head for 20 hours. The cooled mixture was washed with sodium bicarbonate solution (5 ml.), water (2 × 100 ml.) and dried over anhydrous sodium sulphate. The dried solution was evaporated in vacuo to give the title compound (605 mg.) as a pale yellow foam, $[\alpha]_D + 47.2°$ (c 1.11).

Example 57

3α-Hydroxy-2β-(2'-morpholinoethoxy)-5α-pregnane-11,20-dione

2β-(2'-Chloroethoxy)-20,20-ethylenedioxy-3α-hydroxy-5α-pregnan-11-one (500 mg.) was dissolved in morpholine (15 ml.) and the solution heated on a steam-bath for 24 hours. The morpholine was removed by evaporating in vacuo and the resulting red oil was dissolved in 35% aqueous acetic acid (25 ml.). This solution was heated on a steam-bath for 2½ hours. Water (50 ml.) was added and the slightly turbid solution filtered through Kieselguhr. The filtrate was made alkaline with 10N-potassium hydroxide and the precipitate extracted into ether (100 ml.). The ether extract was washed with water until the aqueous layer was neutral, dried over anhydrous sodium sulphate and evaporated to give the title compound as a white foam (250 mg.) $[\alpha]_D + 82°$ (c 0.98).

Example 58

2β-(3'-Chloropropoxy)-20,20-ethylenedioxy-3α-hydroxy-5α-pregnan-11-one

2β-(3'-Chloropropoxy)-3α-hydroxy-5α-pregnane-11,20-dione (470 mg.) was added to a mixture of ethylene glycol (4 ml.), toluene-p-sulphonic acid (3 mg.) and benzene (50 ml.). The vigorously stirred mixture was refluxed under a Dean and Stark head for 17 hours. The cooled mixture was neutralised with sodium bicarbonate solution, ether (50 ml.) added and the organic mixture was washed with water (250 ml.). The organic solution was dried over anhydrous sodium sulphate and evaporated to give the title compound (520 mg.) as a white foam, $[\alpha]_D + 37.5°$ (c 1.03).

Example 59

3α-Hydroxy-2β-(3'-morpholinopropoxy)-5α-pregnane-11,20-dione

2β-(3'-Chloropropoxy)-20,20-ethylenedioxy-3α-hydroxy-5α-pregnan-11-one (500 mg.) was dissolved in morpholine (5 ml.) and the solution heated on a steambath for 8 hours. The solution was poured into water and the precipitate extracted into ether (70 ml.). The ethereal solution was washed with water, dried over anhydrous sodium sulphate and evaporated to a white foam (480 mg.) which was dissolved in 35% aqueous acetic acid and the solution heated on a steam-bath for 3 hours. The solution was cooled in ice and an ice-cooled solution of 10N-potassium hydroxide added to the stirred solution in the presence of ether (100 ml.) until the aqueous layer was basic. The aqueous layer was extracted with ether (50 ml.) and the combined ether extracts washed with water, dried over anhydrous sodium sulphate and evaporated to a white foam (390 mg.) which was purified by preparative TLC in acetone to give the title compound (250 mg.) as a white foam, $[\alpha](c\ D + 65.0°$ (C 1.02).

Example 60

3α-Hydroxy-2β-piperidinoacetoxy-5α-pregnane-11,20-dione, citrate salt

3α-Hydroxy-2β-piperidinoacetoxy-5α-pregnane-11,20-dione (95 mg.) was dissolved in ethanol (2 ml.) and to the solution was added 0.1 molar aqueous citric acid solution (2 ml.). The mixture was evaporated at < 40°, and the residue was dried in vacuo to constant weight. Water (2 ml.) was added, and the mixture was filtered. The solid was washed with water (2 ml.), then dissolved in chloroform and the solution evaporated and dried in vacuo to give a white solid (10 mg.). It was therefore assumed that the aqueous filtrates contained 85 mg. of the steroidal base, and so these were combined and diluted with water to 8.5 ml to give a concentration of 10 mg./ml. with respect to steroid free base.

Example 61

2β-Ethoxy-3α-hydroxy-19-nor-5α-pregnane-11,20-dione

A stirred solution of 3α-hydroxy-19-nor-5α-pregnane-11,20-dione (1.0 g.) in dry pyridine (5 ml.) was treated with toluene-p-sulphonyl chloride (1.0 g.) overnight at room temperature. The resulting solution was partitioned between water (100 ml.) containing 2N-hydrochloric acid (12 ml.) and chloroform. The organic layer was washed, dried (Na₂SO₄) and evaporated to afford the crude tosylate (1.2 g.).

A solution of the crude tosylate in benzene (35 ml.) was run onto grade H alumina and left overnight. Elution of the column with benzene and evaporation of the solvent afforded crude 19-nor-5α-pregn-2-ene-11,20-dione (0.58g.).

A solution of crude 19-nor-5α-pregn-2-ene-11,20-dione (0.58 g.) in "ethanol free" chloroform (8 ml.) was treated with m-chloroperbenzoic acid (0.5 g.) overnight at room temperature. The resulting solution was partitioned between chloroform and dilute aqueous sodium bicarbonate. The organic layer was washed, dried (Na₂SO₄) and evaporated to afford crude 2α,3α-epoxy-19-nor-5α-pregnane-11,20-dione (0.7 g.).

A solution of crude 2α,3α-epoxy-19-nor-5α-pregnane-11,20-dione (0.7 g.) in ethanol (30 ml.) was treated with concentrated sulphuric acid (2 drops.) at room temperature for 15 min. The resulting mixture was partitioned between water and ether and the organic layer was washed with water, dried (Na₂SO₄) and evaporated. The residue was subjected to preparative t.l.c. (EtOAc : CHCl₃ 1 : 3) to afford the title compound (0.2 g.) as a white foam; $[\alpha]_D + 162°$ (c 0.6).

Example 62

2β-n-Butyl-3α-hydroxy-5α-pregnane-11,20-dione

A 2 molar solution of n-butyl lithium in hexane (30 ml., 60mmole) was added to a stirred suspension of cuprous iodide (5.7 g., 30 mmole) in dry ether (90 ml.) under nitrogen at −20°. A cold solution of 2α,3α-epoxy-5α-pregnane-11,20-dione (1.65 g., 5 mmole) in dry ether (260 ml.) was then added and the mixture was maintained at 0° for 70 hr. The reaction mixture was then poured into aqueous ammonium chloride solution and extracted into ethyl acetate.

The organic extract was washed with water, dried (MgSO₄) and evaporated in vacuo. The residue (2.23 g.) was purified by repeated preparative thin layer chromatography to give the title compound (0.21 g.), $[\alpha]_D + 102.5°$ (c 0.5).

Example 63

2β-Acetoxy-3α-hydroxy-5α-pregnane-11,20-dione

2α,3α-Epoxy-5α-pregnane-11,20-dione (500 mg.) was dissolved in glacial acetic acid (25 ml.), and the solution was heated on a steam-bath for 3 hours. Evaporation of the solution under reduced pressure gave an oil which was purified by preparative TLC in ethyl acetate-petrol, and foamed in vacuo to give the title compound as a white foam, $[\alpha]_D + 93.5°$.

Example 64

3α-Acetoxy-2β-bromo-5α-pregnan-20-one

A solution of 3α-hydroxy-2β-bromo-5α-pregnan-20-one (8.5 g.) in pyridine (25 ml.) was treated with acetic anhydride (12.5 ml.), and the mixture was allowed to stand at room temperature overnight. The reaction mixture was poured into water and the product was extracted with methylene chloride. The extract was washed with water, dried (Na₂SO₄) and evaporated. A portion (582 mg.) of the residue (8.5 g.) was purified by preparative thin layer chromatography and crystallisation from iso-propyl ether to give the title compound (70 mg.), m.p. 142°–146°, $[\alpha]_D + 120.9°$.

Example 65

2β-Ethoxy-3α-hydroxy-16α-methyl-5α-pregnane-11,20-dione

A solution of methyllithium in ether (c. 2M 4 ml.) was added to a stirred slurry of cuprous iodide (630 mg.) in dry ether (60 ml.) under dry nitrogen until the initially formed yellow precipitate redissolved. A solution of 2β-ethoxy-3α-hydroxy-5α-pregn-16-ene11,20-dione (420 mg.) in dry tetrahydrofuran (35 ml.) was added to the stirred solution at 0° and stirring was continued, at 0°, for 30 minutes. The mixture was then poured into saturated ammonium chloride solution (150 ml.), more ether (150 ml.) was added, the organic layer separated, washed with saturated ammonium chloride solution (150 ml.) and water (150 ml.) and dried (Na₂ SO₄). The solution was then evaporated. The residue was purified by preparative TLC (CHCl₃ × 4). The least polar component was recrystallised from acetone/petrol to give title compound (130 mg.) as white needles; m.p. 178°–179°; $[\alpha]_D + 112°$ (c 0.3).

Example 66

2β-(2-Cyanoethoxy)-3α-hydroxy-5α-pregnane-11,20-dione

2α,3α-Epoxy-5α-pregnane-11,20-dione (2 g), dry ether (50 ml) and 2-cyanoethanol (10 ml.) were sirred at room temperature until the solid had dissolved. Boron trifluoride diethyl etherate (10 drops) was added. After 2 hours at room temperature a further quantity of etherate (10 drops) was added. After 1 hour further etherate (10 drops) was added and after a further hour, the mixture was neutralised with saturated sodium bicarbonate solution, ethyl acetate (50 ml.) added and the organic layer washed with water (3 × 200 ml.). The washed solution was dried over anhydrous sodium sulphate and evaporated to a white foam which was purified by preparative T.L.C. using ethyl acetate. The main band (Rf 0.4) gave the title compound (740 mg;) m.p. 194°–196°C. $[\alpha]_D + 85°$.

Example 67

2β-(2-ethoxycarbonylethoxy)-3α-hydroxy-5α-pregnane-11,20-dione

2β-(2-Cyanoethoxy)-3α-hydroxy-5α-pregnane-11,20-dione (430 mg) was dissolved in absolute ethanol (50 ml) and dry hydrogen chloride passed through the solution until saturation occurred. The mixture was left for one-fourth hour then poured into water (250 ml.). After one-half hour the precipitate formed was extracted into ether (2 × 100 ml), the ethereal solution washed with water and dried over anhydrous sodium sulphate. The dried solution was evaporated to a white form (320 mg) which was purified by preparative T.L.C. using ethyl acetate/petrol (4/1) run twice. The main band (Rf[0.4) gave title compound (140 mg) as an oil. $[\alpha]_D + 61°$(c, 0.5%).

Example 68

3α-Hydroxy-2β-propionyloxy-5α-pregnane-11,20-dione

2α,3α-Epoxy-5α-pregnane-11,20-dione (500 mg) was dissolved in propionic acid (10 ml) and the solution heated on a steam bath for 5 hours. The mixture was poured into water (200 ml) and the white precipitate extracted into ether. The ethereal solution was washed with 2N-sodium hydroxide solution until the aqueous layer remained basic, then water and then dried over anhydrous sodium sulphate. The dried solution was evaporated to a white foam (560 mg) which was purified by preparative T.L.C. using ethyl acetate/petrol (2/1). The main band (Rf 0.4–0.5) gave title compound (393 mg.) as a white foam. $[\alpha]_D + 84.4°$ (c 1.05).

Example 69

3α-Hydroxy-2β-toluene-p-sulphonyloxy-5α-pregnane-11,20-dione

Toluene-p-sulphonic acid (550 mg) was refluxed in benzene (20 ml) under a Dean and Stark head for one-half hour. The solution was cooled to room temperature, the acid crystallising out, ether (20 ml) added and the mixture stirred until the crystals had redissolved. A mixture of 2α,3α-epoxy-5α-pregnane-11,20-dione (1 g) and ether (10 ml) was added and the reaction stirred at room temperature for 14 hours. The mixture was poured into water, the organic layer separated and the aqueous layer extracted with ether (50ml.) The combined organic extracts were washed with sodium bicarbonate solution, water (100 ml) and dried over anhydrous sodium sulphate. The dried solution was evaporated to give title compound (1.32 g) as a white foam, $[\alpha]_D + 52°$ c 0.94).

Example 70

2β-Azido-3α-hydroxy-5α-pregnane-11,20-dione a. 2α,3α-Epoxy-5α-pregnane-11,20-dione (500 mg) was dissolved in dimethylsulphoxide (25 ml) and sodium azide (1.5 g) added to the solution. Concentrated sulphuric acid (10 drops) was added and the mixture heated on a steam bath for 48 hours. The solution was poured into iced water (600 ml) and the precipitate extracted into ether (100 ml). The ether extract was washed with water (4 + 250 ml) and then saturated sodium bicarbonate solution (250 ml) and finally water (250 ml.). The organic solution was dried over anhydrous sodium sulphate and evaporated to a white foam which was purified by preparative T.L.C. using ethyl acetate/petrol (1/1) run twice. The main band gave title compound (290 mg;) as a foam, $[\alpha]_D + 95°$ (c, 0.98).

b. 2α,3α-epoxy-5α-pregnane-11,20-dione (1 g) was added to a mixture of sodium azide (1g), boric acid (1g) and dimethylformamide (20 ml) and the mixture refluxed for 5 hours. The mixture was cooled, poured into water and the resulting emulsion extracted into methylene chloride (2 × 150 ml.). The organic extracts were washed with water (2 × 300 ml.) dried over anhydrous sodium sulphate and evaporated to a red oil which was purified by preparative T.L.C. using ethyl acetate/petrol (1/1), the main band giving 2β-azido-3α-hydroxy-5α-pregnane-11,20-dione (580 mg) as a foam.

c. 3α-hydroxy-2β-toluene-p-sulphonyloxy-5α-pregnane-11,20-dione (500 mg) was dissolved in dimethylsulphoxide (20 ml) and sodium azide (1.5 g) added to the solution. The mixture was heated on a steam bath for 30 hours, cooled and poured into water. The precipitate formed was filtered off, dissolved in ether and the solution dried over anhydrous sodium sulphate. The dried solution was evaporated to a foam (300 mg) which was purified by preparative T.L.C. using ethyl acetate/petrol (1/1). The main band (Rf 0.2-0.3) giving title compound (200 mg) as a foam, $[\alpha]_D + 104°$ (c 0.93), identical with the above compound.

Example 71

2β-Ethoxy-3α-hydroxy-5α-pregnane-11,20-dione, 3-hemisuccinate

Succinic anhydride (220 mg.) was added to a solution of 2β-ethoxy-3α-hydroxy-5α-pregnane-11,20-dione (220 mg.) in dry pyridine (2.2 ml.). The stirred solution was refluxed gently (oil bath temperature 130°) for 5 hours, and then poured into water (20 ml.). The mixture was acidified with dilute hydrochloric acid and extracted with chloroform. The extract was washed with water, dried over sodium sulphate and evaporated to an oil which was purified by preparative T.L.C. in ethyl acetate to give title compound (129 mg) as a foam which collapsed to a gum on standing, $[\alpha]_D + 89°$ (c 0.41).

Example 72

3α-N,N-Dietylaminoacetoxy-2β-ethoxy-5α-pregnane-11,20-dione

2β-Ethoxy-3α-hydroxy-5α-pregnane-11,20-dione (1 g) was dissolved in methylene chloride (5 ml) and pyridine (1 ml.). Chloroacetic anhydride (1 g) was added to the solution and the mixture left at room temperature overnight, the solution becoming deep red and containing a brown precipitate. The mixture was poured into water, methylene chloride added and the organic layer washed with very dilute sulphuric acid, water and dried over anhydrous sodium sulphate. The dried solution was evaporated to a yellow foam which was chromatographed on a silica (30 g) column using chloroform, the first 150 ml. containing 3α-Chloroacetoxy-2β-ethoxy-5α-pregnane-11,20-dione (910 mg.) as a white foam.

3α-Chloroacetoxy-2β-ethoxy-5α-pregnane-11,20-dione (450 mg) was dissolved in acetone (50 ml) and sodium iodide (460 mg) added to the solution. The mixture was refluxed for one-half hour, a white precipitate forming. The precipitate was filtered off and the filtrate evaporated to a yellow foam which ws partitioned between ether and water. The ethereal solution was dried over anhydrous sodium sulphate and evaporated to give 2β-ethoxy-3α-iodoacetoxy-5α-pregnane-11,20 -dione (460 mg) as a pale yellow foam.

2β-Ethoxy-3α-iodoacetoxy-5α-pregnane-11,20-dione (460 mg) was dissolved in methylene chloride (25 ml) and diethylamine (1 ml) added to the solution. The mixture was stirred at room temperature for one-half hour. The mixture was poured into water and the organic layer washed with water (100 ml.), dried over anhydrous sodium sulphate and evaporated to a red oil (410 mg.) which was purified by preparative T.L.C. using ethyl acetate/petrol (2/1) run twice. The main band (RF 0.4) gave title compound (230 mg) as a pale yellow oil $[\alpha]_D + 100°$ (c = 0.9).

Example 73

3α-Hydroxy-2β-methoxy-16β-methyl-5α-pregnane-11,20-dione

3α-Hydroxy-2β-methoxy-16-methyl-5α-pregn-16-ene-11,20-dione (187 mg.) in ethyl acetate (50 ml.) was hydrogenated over 10% palladium-on-carbon catalyst (60 mg.) at atmospheric pressure for 20 minutes, during which time 11 ml. of hydrogen was taken up. The catalyst was filtered off and the filtrate evaporated to a white foam (190 mg.) which was purified by preparative T.L.C. in ethyl acetate/petrol 3/2, run 3 times, to give 88 mg. of impure product which was purified by preparative T.L.C. in ethyl acetate/benzene (1/1) and recrystallisation from ether/petrol to give title compound (68 mg.) as fine white crystals, m.p. 180°–182°, $[\alpha]_D + 69.5°$ (c 0.2).

Example 74

2β-Acetylthio-3α-hydroxy-5α-pregnane-11,20-dione

2α,3α-Epoxy-5α-pregnane-11,20-dione (450 mg.) in dry ether (4 ml.) and thioacetic acid (1 ml.) was treated with BF₃ etherate (2 drops). The resulting yellow solution was stirred at room temperature for 20 minutes. The solution was partitioned between ethyl acetate (20 ml.) and water (20 ml.) and the aqueous layer was extracted with more ethyl acetate (20 ml.). The combined organic extracts were washed with water (2 × 20 ml.) and dried over sodium sulphate and evaporated to a yellow oil which was purified by preparative t.l.c., in ethyl acetate/petroleum ether (1:1) to give the title compound as a pale yellow foam. $[\alpha]_D + 93°$ (c 0.56); $R_f$ 0.15; N.M.R.:–7.65τ (CH₃COS—); 6.16τ (2— and 3—H).

Example 75

0.011 g. of 3α-hydroxy-2β-methoxy-5α-pregnane-11,20-dione were dissolved in 2ml. of acetone at 20°C. The resulting solution was added to 1 g. of Cremophor EL at 20°C. and stirred until homogeneous. The acetone was removed by a vigorous stream of nitrogen. The solution was diluted with sterile distilled water containing 0.025 g. of sodium chloride to give a final volume of 5 ml.

Example 76

0.028 g. of 2β,3α-dihydroxy-5α-pregnane-11,20-dione were dissolved in 2 ml. of acetone at 20°C. The resulting solution was added to 1 g. of Cremophor EL at 20°C. and stirred until homogeneous. The acetone was removed by a vigorous stream of nitrogen. The solution was diluted with sterile distilled water containing 0.025 g. of sodium chloride to give a final volume of 5 ml.

Example 77

0.0148 g. of 2β-chloro-3α-hydroxy-5α-pregnane-11,20-dione were dissolved in 2 ml. of acetone at 20°C. The resulting solution was added to 1 g. of Cremophor EL at 20°C. and stirred until homogeneous. The acetone was removed in a vigorous stream of nitrogen. The solution was diluted with sterile distilled water containing 0.025 g. of sodium chloride to give a final volume of 5 ml.

The following preparations illustrate the preparation of starting materials used in preparing certain compounds according to the invention.

Preparation 1.

2α,3α-Epoxy-5α-pregn-16-ene-11,20-dione

To a solution of 5α-pregna-2,16-diene-11,20-dione (2.5 g.) in chloroform (50 ml.) was added m-chloroperoxybenzoic acid (85%, 1.8 g.), and the mixture was stirred at room temperature overnight. More chloroform was then added, and the solution was washed with dilute sodium bicarbonate solution and with water, dried over magnesium sulphate and evaporated to an oil which was triturated with ether/petrol to give title compound (1.9 g.) as colourless needles, m.p. 154°–156°, $[\alpha]_D + 100°$.

Preparation 2.

2β-Chloro-3α-hydroxy-5α-pregn-16ene-11,20-dione

2α,3α-Epoxy-5α-pregn-16-ene-11,20-dione (250 mg.) in chloroform (10 ml.) was shaken with concentrated hydrochloric acid (8 ml.) for 30 minutes. More chloroform was added, and the organic solution was washed with water, sodium bicarbonate solution and water. It was then dried over magnesium sulphate and evaporated to give a colourless oil which was recrystallised from methanol to give title compound (160 mg.) as colourless prisms, m.p. 209°–212° (decomp.), $[\alpha]_D + 83°$, $\lambda_{max}$ 234 nm ($\epsilon$ 8,350) (EtOH).

Preparation 3.

3α-Hydroxy-2β-methoxy-5α-pregn-16-ene-11,20-dione

2α,3α-Epoxy-5α-pregn-16-ene-11,20-dione (500 mg.) was dissolved in methanol (25 ml.) and to the stirred solution was added concentrated sulphuric acid (0.1 ml). The solution was stirred at room temperature for 15 minutes, then 10% potassium bicarbonate solution (5 ml.) was added, and the mixture was poured into water. The precipitate was extracted into chloroform, and the extract was dried over sodium sulphate and evaporated to an oil which was recrystallised from ethyl acetate/petrol to give title compound (370 mg.) as fine white crystals, m.p. 159°–163°, $[\alpha]_D + 82.0°$.

Preparation 4.

2α,3α-Epoxy-5α-pregn-16-en-20-one a. 3β-Toluene-p-sulphonyloxy-5α-pregn-16-en-20-one 3β-Hydroxy-5α-pregn-16-en-20-one (10 g.) in pyridine (50 ml.) was treated with toluene-p-sulphonyl chloride (10 g.), and the solution was stirred at room temperature overnight and then poured into dilute hydrochloric acid. The precipitate was extracted into chloroform, and the extract was washed with dilute hydrochloric acid and with water, dried over sodium sulphate and evaporated to an oil which crystallised on standing. Recrystallisation from ethyl acetate/petrol gave 3β-toluene-p-sulphonyloxy-5α-pregn-16-en-20-one (13.3g) as off-white prisms, m.p. 146°–148°, [α]$_D$ + 24.0°, λ$_{max}$. (EtOH) 226.5 nm (ε 18,600), 240 nm (infl.) (ε 9550), 272.5 nm (ε 518).

b. 5α-Pregna-2,16-diem-20-one

3β-Toluene-p-sulphonyloxy-5α-pregn-16-en-20-one (6 g.) was added to hot collidine (12 ml.), and the solution was then refluxed for 30 minutes. The solution was allowed to cool and then poured into cold dilute hydrochloric acid. The precipitate was filtered off, washed with water and dissolved in methylene chloride. The solution was dried over sodium sulphate and then filtered through a short column of silica gel (50 g.). The methylene chloride eluate (about 150 ml.) was evaporated to give 5α-pregna-2,16-dien-20-one (3.29 g.) as white crystals, m.p. 143°–145°, [α]$_D$ + 110.5°.

c. 2α,3α-Epoxy-5α-pregn-16-en-20-one

5α-Pregna-2,16-dien-20-one (3.0 g.) in chloroform (50 ml.) was treated with m-chloroperbenzoic acid (85%, 2.0 g.). The solution was stirred at room temperature overnight, diluted with more chloroform (50 ml.), washed with dilute potassium bicarbonate solution and with water, dried over sodium sulphate and evaporated to an oil which crystallised on standing. Recrystallisation from ethyl acetate/petrol gave title compound (2.75 g.) as colourless plates, m.p. 145°–149° [α]$_D$ + 74.5°, λ$_{max}$. 238 nm (ε 8970).

Preparation 5

2β-Chloro-3α-hydroxy-5α-pregn-16-en-20-one

2α,3α-Epoxy-5α-pregn-16-en-20-one (500 mg.) was dissolved in methylene chloride (15 ml.) and concentrated hydrochloric acid (12 ml.) was added. The mixture was shaken for 20 minutes, and then poured into water (100 ml.) and chloroform (100 ml.). The organic layer was separated, washed well with water, dried over sodium sulphate and evaporated to an oil. Recrystallisation from ethyl acetate gave title compound (447 mg.) as colourless crystals, m.p. 246°–252°, [α]$_D$(c, 1.10)+ 65.8°, λ$_{max}$. (EtOH) 239 nm (ε 8770).

Preparation 6

3α-Hydroxy-2β-methoxy-5α-pregn-16-en-20-one

2α,3α-Epoxy-5α-pregn-16-en-20-one (500 mg.) in methanol (30 ml.) was treated with concentrated sulphuric acid (0.1 ml.). The reaction solution was stirred at room temperature for 10 minutes, and then potassium bicarbonate solution (10%, 6 ml.) and water were added and the precipitate was extracted into chloroform. The chloroform solution was evaporated to an oil which was purified by preparative TLC in ethyl acetate/petrol (1/2), to give, as the major product title compound (255 mg) as colourless plates (from ethyl acetate/petrol), m.p. 186°–189°, [α]$_D$ (c, 0.82) + 62°, λ$_{max}$ (EtOH) 239 nm (ε 8370).

Also isolated was 2β,16α-dimethoxy-3α-hydroxy-5α-pregnan-20-one (42 mg.) as colourless needles (from ethyl acetate/petrol). m.p. 183°–187°.

Preparation 7 a. 3β-Hydroxy-5α-pregn-16-ene-11,20-dione

A solution of 3β-acetoxy-5α-pregn-16-ene-11,20-dione (Chamberlin et al., J. Amer. Chem. Soc., 1951, 73, 2396) (25.7 g.) in dioxan (500 ml.) was treated with potassium hydroxide (10 g.) and water 250 ml. and the mixture allowed to stand at room temperature for 1 hour. After a further 1 hour at 40° the mixture was diluted with water and the product filtered off. The crude material was dissolved in chloroform and filtered through a column of grade III neutral alumina (ca. 100 g.). The material obtained was crystallised from acetone petroleum to give pure title compound (17.65 g.), as small plates, m.p. 217.5°, [α]$_D$ +82.9° (c 1.1), λ$_{max}$. 234 nm. (ε 10,100).

b. 3β-Toluene-p-sulphonyloxy-5α-pregn-16-ene-11,20-dione

A solution of 3β-hydroxy-5α-pregn-16-ene-11, 20-dione (39.6g) in dry pyridine (165 ml.) was treated with toluene-p-sulphonyl chloride (43.9 g.) to give the toluene sulphonate (56.7 g.) m.p. 147°-151°. A portion (10.7 g.) of this material was crystallised from ethyl acetate-petroleum to give the pure toluene sulphonate (9.2 g.) as plates m.p. 154°–155°, [α]$_D$ + 42.8°(c, 1.2), λ$_{max}$. 226 nm (ε20,780).

c. 3α-Hydroxy-5α-pregn-16-ene-11,20-dione and 5α-pregna-2,16-diene-11,20-dione

A stirred mixture of 3β-toluene-p-sulphonyloxy-5α-pregn-16-ene-11,20-dione (627 g.), potassium acetate (918 g.), dimethylformamide (4.25 l.) and water (425 ml.) was heated on the steam bath for 4 hr. Most of the dimethylformamide was removed under reduced pressure and water was added to the residue with stirring. The solid (420 g.) was collected, washed and dried at 40° in vacuo. This material in peroxide free dioxan (7 l.) was flushed with nitrogen and a solution of potassium hydroxide (200 g.) in water (2 l.) was added. The mixture was stirred and heated at 50°–60° for 7 hr. and then left at room temperature overnight. Acetic acid (50 ml.) was added and the precipitated solid was filtered off, washed with water and dried. The dry solid was heated under reflux with benzene (2 l.) for 2 hr. the mixture cooled and filtered to give 3α-hydroxy-5α-pregn-16-ene-11,20-dione (215 g.).

Benzene extracts from several similar experiments were combined and evaporated. The crude solid was redissolved in hot benzene and petroleum was added until the solution was just clear at ambient temperature, (an insoluble residue was removed by filtration at this stage). The clear solution was passed down an alumina column (Woelm alumina activity grade I) previously prepared with benzene-petroleum in the ratio 6:4. Elution with the same solvent gave the diene. Elution was terminated when thin layer chromatography indicated the presence of slower running components in the eluate. The combined fractions were evaporated and twice crystallised from benzene-petroleum to give 5α-pregna-2,16-diene-11,20-dione as colourless crystals, m.p. 176°–177°, [α]$_D$ + 159° λ$_{max}$ (EtOH) 233.5 nm (ε 9150).

Preparation 8

2β-Ethoxy-3α-hydroxy-5α-pregn-16-ene-11,20-dione.

2α, 3α-Epoxy-5α-pregn-16-ene-11,20-dione (3 g.) was dissolved with warming in dry ethanol (80 ml.). The solution was stirred and allowed to cool to room temperature. Concentrated sulphuric acid (0.7 ml.) was added and the solution was stirred at room temperature for 30 minutes. Potassium bicarbonate solution (10%, 35 ml.) was added and the mixture poured into ice-cold water (1 liter) and extracted with chlorform (2

× 200 ml.). The extract was dried over sodium sulphate and evaporated to a colourless oil (2.73 g.) which was purified by preparative TLC in ethyl acetate/petrol 1/1, the plates being run 3 times and the main UV-absorbing, band separated and recrystallised from ethyl acetate/ petrol to give title compound (950 mg.) as fine white crystals, m.p. 89-91° $[\alpha]_D \pm 77°$ c 0.3).

Preparation 9 a. (16β-H)-1'-Pyrazolino-(4',3':16α, 17α)-5α-pregn-2-ene-11,20-dione

5α-Pregna-2,16-diene-11,20-dione (2.0 g.) in dry tetrahydrofuran (40 ml.) was treated with an excess of ethereal diazomethane and the yellow solution was left at room temperature overnight. The unreacted diazomethane was removed by adding two drops of glacial acetic acid. The solution was evaporated to a crystalline residue which was recrystallised from acetone/petrol to give title compound (2.07 g.) as white needles, m.p. 160°-161° (with nitrogen evolution), $[\alpha]_D$ +200° (c. 1.17).

b. 16-Methyl-5α-pregna-2,16-diene-11,20-dione.

(16β-H)-1'-Pyrazolino-(4',3':16α,17α)-5αpregn-2-ene-11,20-dione (2.29 g.) was added gradually to dimethylformamide (10 ml.) at 150°, nitrogen being evolved. The reaction solution was kept at 150° for 10 minutes, and then left to cool. Water (20 ml.) was added and the white suspension was extracted with methylene chloride (3 × 25 ml.). The extracts were combined, washed with water (75 ml.), dried over sodium sulphate and evaporated to a cream-coloured solid. Recrystallisation from petrol containing a little acetone gave title compound (840 mg.) as white crystals, m.p. 191°-194°, $[\alpha]_D$ + 75° $\lambda_{max}$ (EtOH) 247 nm (ε9250).

c. 2α,3α-Epoxy-16-methyl-5α-pregn-16-ene-11,20-dione

16-Methyl-5α-pregna-2,16-diene-11,20-dione (800 mg.) in methylene chloride (50 ml.) was treated with m-chloroperbenzoic acid (85%; 535 mg.), and the solution was left to stand at room temperature overnight. More methylene chloride (50 ml.) was added and the solution washed with potassium bicarbonate solution (5%, 100 ml.) and with water (100 ml.), dried over sodium sulphate and evaporated to a crystalline solid (~ 1g.) which was purified by preparative TLC in ethyl acetate/petrol, 1/1 run twice. The main band yielded a white solid (650 mg.) which was recrystallised from acetone/ petrol to give title compound (515 mg.) as white crystals, m.p. 155°-157°, $[\alpha]_D$ + 57.8° (c 0.9), $\lambda_{max. (EtOH)}$ 246.5 nm (ε 9150).

d. 3α-Hydroxy-2β-methoxy-16-methyl-5α-pregn-16-ene-11,20-dione

2α,3α-Epoxy-16-methyl-5α-pregn-11,20 -dione (500 mg.) was dissolved in dry methanol (25 ml.) and to the stirred solution was added concentrated sulphuric acid (0.1 ml.). After 10 minutes, potassium bicarbonate solution and icewater were added and the fine precipitate (600 mg.) was filtered off and purified by preparative TLC in ethyl acetate, the main band ($R_f$ 0.5) being recrystallised from acetone/petrol to give title compound (365 mg.) as white crystals, m.p. 184°-186°, $[\alpha]_D$ + 51.6° $\lambda_{max.}$ (EtOH) 247 nm (ε 9100).

Preparation 10

11α-Hydroxy-19-norpregna-4,16-diene-3,20-dione

A solution of a mixture of 11α,17α-dihydroxy-19-norpregn-4-ene-3,20-dione (4 g.) and semicarbazide hydrochloride (4 g.) in methanol (200 ml.) was refluxed for 2 hr. The methanol was then removed by distillation under reduced pressure and water was added to the residue. The precipitated solid was collected by filtration, washed with water and dried over $P_2O5$ in vacuo. A solution of this solid in a mixture of glacial acetic acid (80 ml.), water (28 ml.) and pyruvic acid (4 ml.) was heated on a steam bath for 1 hr. The resulting solution was concentrated under reduced pressure and partitioned between saturated aqueous sodium bicarbonate and ethyl acetate. The organic layer was washed with water, dried ($Na_2 SO_4$) and evaporated to dryness. The residue was subjected to preparative, T.L.C. ($CHCl_3$, $(CH_3)_2$ CO; 15 : 1) and crystallised from acetone/petroleum ether to afford title compound (1.6 g.) as white needles, m.p. 149°.

Preparation 11

19-nor-5α-pregna-3,11,20-trione via 3ξ, 11α-20ξ-trihydroxy-19-nor-5α-pregnane

A solution of 11α-hydroxy-19-norpregna-4,16-diene-3,20-dione (2.5 g.) in dry tetrahydrofuran (200 ml.) was added over 5 mins. to a solution of lithium (5 g.) in liquid ammonia (2.5 liters). The solutuon was then left for 30 min. Ethanol (ca. 100 ml.) was then added until the blue colour had been discharged and the ammonia was then allowed to evaporate. The residue was partitioned between water and ether. The organic layer was washed, dried ($Na_2 SO_4$) and evaporated to give crude 3ε, 11α,20ε-trihydroxy-19-nor-5α-pregnane (1.5 g.). The crude trihydroxy compound was oxidised in two ways.

a. Acidic potassium dichromate.

A solution of crude 3ε,11α-20ε-trihydroxy-19-nor-5α-pregnane (4 g.) in acetone (280 ml.) was treated with a solution of potassium dichromate (8.0 g.) in 2N-sulphuric acid (38 ml.) at room temperature for 1 hr. An additional quantity of potassium dichromate (8 g.) in 2N-sulphuric acid (38 ml.) was then added and left at room temperature for 15 mins. The solution was then partitioned between water and ether and the organic layer was washed with water, dried ($Na_2 SO_4$) and evaporated. The residual oil was subjected to preparative T.L.C. ($CHCl_3$) and recrystallised from acetone/petroleum ether to afford title compound (1.04 g.) as white prisms, m.p. ° $[\alpha]_D$ + 240° (c 1.0).

b. Jones Reagent.

A solution of crude 3ε,11α,20ε-trihydroxy-19-nor-5α-pregnane (1.5 g.) in acetone (40 ml.) was treated dropwise with Jones reagent (5 ml.) [a solution of chromium trioxide (267 g.) in a mixture of concentrated sulphuric acid (230 ml.) and water (400 ml.) made up to 1 liter with water (8N w.r.t. oxygen)] at room temperature The resulting solution was partitioned between water and ethyl acetate. The organic layer was washed with water, dried ($Na_2 SO_4$) and evaporated. The residue was subjected to preparative T.L.C. $CHCl_3$, and recrystallised from acetone/petroleum ether to afford the title compound (0.44 g.).

Preparation 12

3α-hydroxy-19 nor -5α-pregnane-11,20-dione

A solution of 19-nor-5α-pregnane-3,11,20-trione (0.9 g.) in chloroiridic solution (75 ml.) [prepared by refluxing a mixture of chloroiridic acid (0.09 g.), 90% isopropyl alcohol (200 ml.) and trimethyl phosphite (16 ml.) for 16 hr. The solution was neutrallised with triethylamine immediately prior to use] was refluxed for 24 hr. The solution was then cooled, partitioned between water and ether and the organic layer was washed with water, dried ($Na_2 SO_4$) and evaporated. The residue was subjected to preparative T.L.C. (EtOH) was recrystallised from to afford the title compound (0.6 g.) or white needles, m.p. 154°, $[\alpha]_D + 200°$ (c 1.0).

Example 78

2β-Ethylthio-3α-hydroxy-5α-pregnane-11,20-dione

2α,3α-Epoxy-5α-pregnane-11,20-dione (50 mg.) in dry ether was treated with ethanethiol (0.8 mls.) and $BF_3$ etherate (3 drops). The reaction mixture was stirred at room temperature for 20 minutes; then ether (5 mls.) and potassium bicarbonate solution (10%, 2.5 ml.) were added. The ether layer was evaporated to about 5 mls. and purified by preparative t.l.c. in ethyl acetate/petroleum ether (2:1) to give a colourless oil (200 mgs.) which was triturated with acetone and petroleum ether to give the title compound (174mg); fine white crystals; m.p. 170°–173°; $[\alpha]_D + 93°$ (c 0.6).

We claim:

1. A pharmaceutical composition comprising a compound of the formula

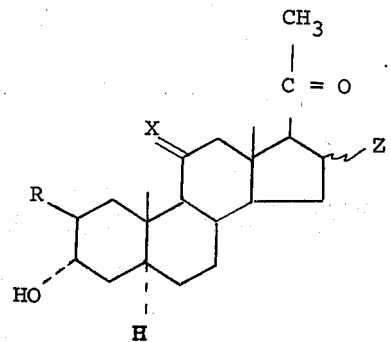

wherein:
R is a chlorine atom or thiocyanato;
X is 2 hydrogen atoms or an oxo group; and
Z is 2 hydrogen atoms, a hydrogen atom and a chlorine atom, or a hydrogen atom and methyl together with a pharmaceutical carrier or excipient.

2. A composition according to claim 1 in which said compound is 2β-chloro-3α-hydroxy-5α-pregnane-11,20-dione.

3. A composition according to claim 1 in which said compound is 2β-thiocyanato-3α-hydroxy-5α-pregnane-11,20-dione.

4. A method of inducing anaesthesia comprising administering parenterally to a subject to be anaesthetized an effective amount of a compound of the formula

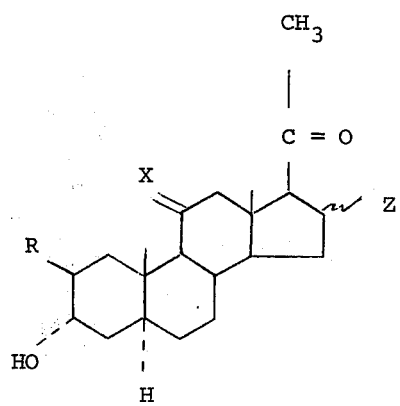

wherein:
R is a chlorine atom or thiocyanato;
X is 2 hydrogen atoms or an oxo group; and
Z is 2 hydrogen atoms, a hydrogen atom and a chlorine atom, or a hydrogen atom and methyl.

5. A composition according to claim 1 in the form of an anaesthetic composition suitable for use by parenteral administration, wherein the carrier or excipient is a parenterally acceptable vehicle.

6. A method according to claim 4 which comprises administration of from 0.25 to 3.5 mg/kg of said compound.

7. A method according to claim 6 in which said compound is 2β-chloro-3α-hydroxy-5α-pregnane-11,20-dione.

8. A method according to claim 6 in which said compound is 2β-thiocyanato-3α-hydroxy-5α-pregnane-11,20-dione.

* * * * *